United States Patent
Marinow

(10) Patent No.: US 8,755,872 B1
(45) Date of Patent: Jun. 17, 2014

(54) PATIENT MONITORING SYSTEM FOR INDICATING AN ABNORMAL CONDITION

(75) Inventor: Nikolai Marinow, Herrenberg (DE)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 13/560,857

(22) Filed: Jul. 27, 2012

Related U.S. Application Data

(60) Provisional application No. 61/512,525, filed on Jul. 28, 2011.

(51) Int. Cl.
*A61B 5/0452* (2006.01)
(52) U.S. Cl.
USPC .......................................................... 600/509
(58) Field of Classification Search
USPC .......................................................... 600/517
See application file for complete search history.

(56) References Cited

U.S. PATENT DOCUMENTS

| | | | |
|---|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |

(Continued)

*Primary Examiner* — Michael Kahelin
(74) *Attorney, Agent, or Firm* — Knobbe, Martens, Olson and Bear, LLP

(57) ABSTRACT

A patient monitor in communication with ECG leads is configured to monitor physiological parameters over time to indicate an abnormal condition. The physiological parameters can include an ST parameter and/or action potential, and the abnormal condition can be an anaerobic state. To identify the abnormal condition, the patient monitor identifies a reference physiological parameter measurement of a patient at a first time and determines expected physiological parameter measurements based on different heart rates. The patient monitor compares an expected physiological parameter measurement of a patient at a current heart rate with an actual physiological parameter measurement at the current heart rate. The patient monitor indicates an abnormal condition if the difference between the expected and actual physiological parameter measurement is greater than a threshold amount.

28 Claims, 12 Drawing Sheets

(56) References Cited

U.S. PATENT DOCUMENTS

| | | | |
|---|---|---|---|
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |

(56) References Cited

U.S. PATENT DOCUMENTS

| | | |
|---|---|---|
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,254,440 B1 * | 8/2007 | Kroll .......................... 600/517 |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,558,623 B2 * | 7/2009 | Fischell et al. ................ 600/517 |
| 7,563,110 B2 | 7/2009 | Al-Ali et al. |
| 7,596,398 B2 | 9/2009 | Al-Ali et al. |
| 7,618,375 B2 | 11/2009 | Flaherty et al. |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |

(56) References Cited

U.S. PATENT DOCUMENTS

| | | |
|---|---|---|
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 2004/0215092 A1* | 10/2004 | Fischell et al. .............. 600/515 |
| 2010/0217144 A1* | 8/2010 | Brian ......................... 600/523 |

\* cited by examiner

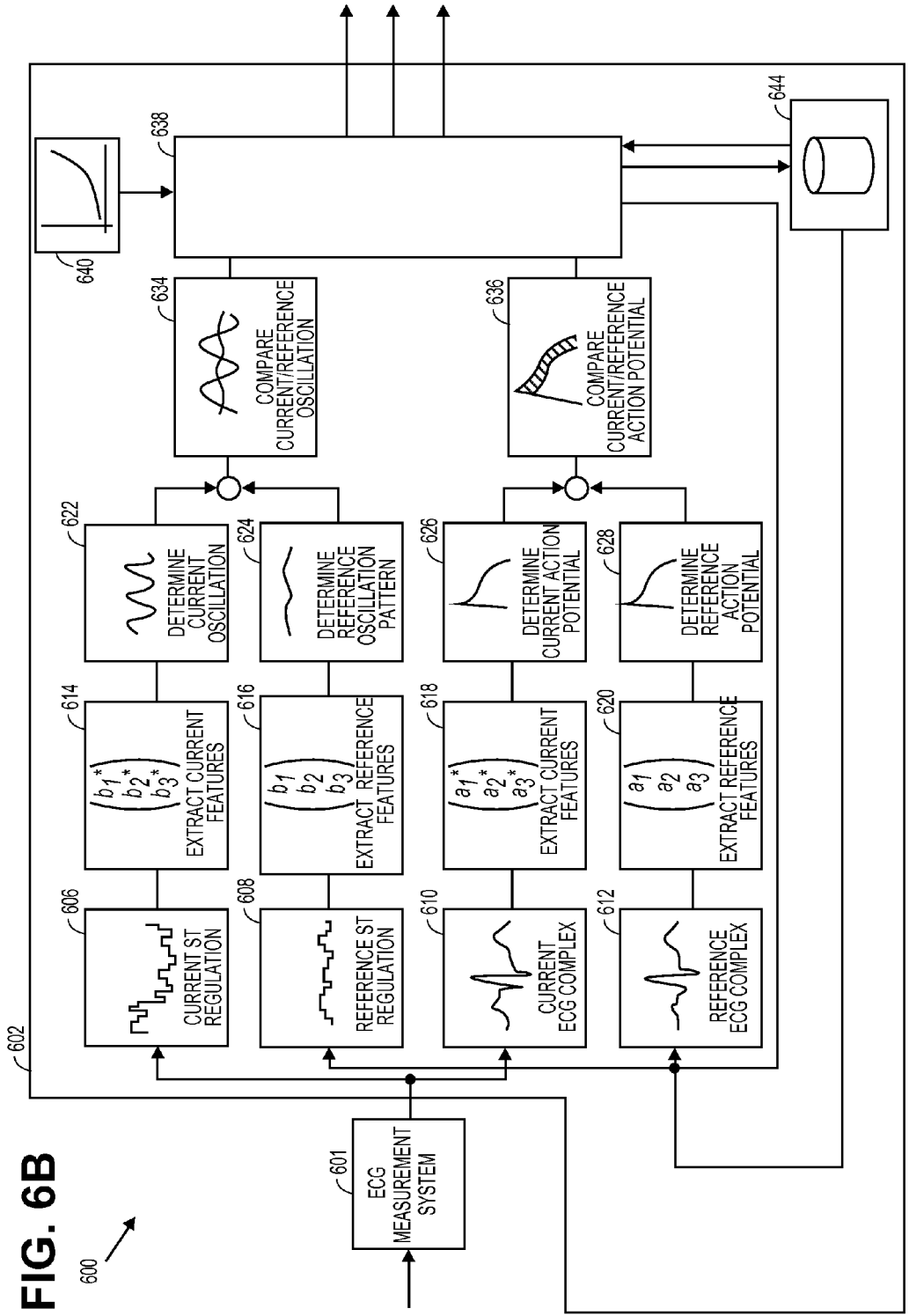

PATIENT MONITORING SYSTEM FOR INDICATING AN ABNORMAL CONDITION

RELATED APPLICATIONS

The present application claims priority benefit from U.S. App. 61/512,525 entitled PATIENT MONITORING SYSTEM FOR INDICATING AN ABNORMAL CONDITION, filed Jul. 28, 2011, which is hereby incorporated by reference herein in its entirety.

BACKGROUND

Healthcare facilities typically monitor many different physiological parameters of a patient while the patient is admitted to determine the patient's condition. Additional medical attention is not typically provided unless one of the measured physiological parameters deviates abnormally or the patient exhibits a serious condition. However, despite all the monitored physiological parameters, a patient's condition can deteriorate over time without being detected. The patient's deteriorating condition may take from minutes up to several hours and go unnoticed until it becomes an emergency. In some instances, the patient enters an undetected anaerobic state. By the time the patient's condition is detected, the patient may require emergency medical attention, or even worse, may die. Further, the inability to detect the patient's deteriorating condition can increase the length of stay of the patient, leading to increased medical bills and hospital costs.

Outside of ICU early patient mobilization contributes to improved patient recovery. Dependent on the disease, some patients can have a very low anaerobic threshold e.g. chronic disease like (Chronic Obstructive Pulmonary Disease), cardiac patients with angina pectoris, coronary bypass surgery patients required to rest for considerable time and all patients with compromised peripheral perfusion, among others. In cardiac rehabilitation, regular patient exercise can be a key element of therapy for successful recovery. Up until now it has been challenging to find a "safe training range" for such patients. To avoid potentially dangerous situations during exercise of cardiac rehab patients, training instructors keep the exertion level rather low.

In addition, athletes seeking to improve their conditioning want to train near their anaerobic threshold without passing it. To know the level at which they should train, the athletes want to know their anaerobic threshold. Typically, multiple blood samples are taken during increased levels of training to obtain information regarding the athlete's anaerobic threshold. Blood tests are then performed on the samples to indicate the point at which the athlete passed the anaerobic threshold and entered an anaerobic state. Taking multiple blood samples while an athlete is training can be burdensome and time consuming. Furthermore, the athlete must wait for the blood test results to know their anaerobic threshold and modify their training regime.

SUMMARY

A patient monitoring system is configured to monitor various physiological parameters over time to indicate an abnormal condition. The physiological parameters can include ST parameters and/or cardiac action potential parameters. The ST parameters can include ST regulation pattern, ST measurement, average ST measurement, ST mean deviation, ST oscillation pattern, ST variation, average ST measurement/HR etc. The cardiac action potential parameters can include cardiac action potential amplitude, duration, calcium influx duration, JT/HR ratio, etc. Cardiac action potential can also be referred to as action potential. The patient monitoring system can include a plurality of electrocardiogram (ECG) leads and a patient monitor.

The patient monitor identifies one or more reference physiological parameter measurements and a first heart rate at a first time using data from the ECG leads. The first time can be when a patient is at rest, such as when the patient is sitting or lying down. The patient monitor determines a second heart rate of the patient at a second time. The patient monitor can use data from the ECG leads to determine the second heart rate. The patient monitor also determines an expected physiological parameter measurement. The patient monitor can determine the expected physiological parameter measurement based on the second heart rate. The patient monitor can also use the reference physiological measurement to determine the expected physiological parameter measurement. The patient monitor determines a second physiological parameter measurement at the second heart rate and compares the expected physiological parameter measurement with the second physiological parameter measurement. Based on the comparison, the patient monitor determines whether an abnormal condition exists. In an embodiment, the patient monitor can determine that an abnormal condition exists upon determining that the difference between the expected physiological parameter measurement and the current physiological parameter measurement exceeds a threshold value.

BRIEF DESCRIPTION OF THE DRAWINGS

FIG. 6B is a diagram illustrative of the interaction between the various components of a patient monitoring system configured to determine a patient's status based on one or more physiological parameters.

DETAILED DESCRIPTION

Figure 1A:
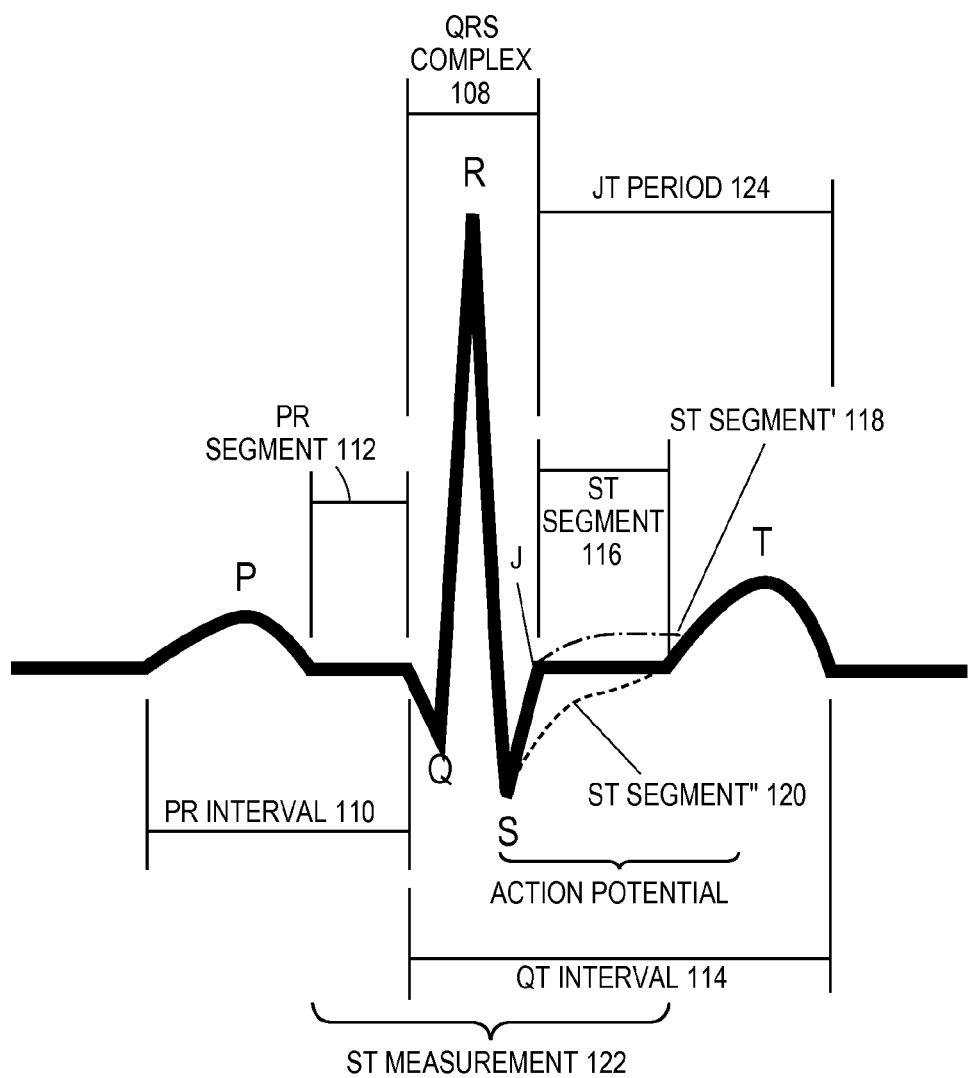
FIG. 1A is a schematic diagram of an embodiment of an electrocardiogram (ECG) waveform.

A patient monitoring device, in communication with ECG sensors, monitors the ST regulation pattern data within an ECG complex as well as action potential data retrieved from the ECG sensors. The ST regulation pattern, also referred to as ST regulation, and action potential data can each be represented by a template within a time interval. The ST regulation pattern data can include data from one or more ST regulation patterns from one or more ECG sensors. By monitoring ST regulation and action potential the patient monitor is able to identify abnormal patient conditions before they become serious. The patient monitor indicates the abnormal condition to healthcare providers who are able to treat the abnormal condition before it becomes an emergency, thereby reducing a patient's length of stay and healthcare costs, and improving the survivability of patients. In addition, the patient monitoring device can accompany a mobile patient and monitor the patient's condition while the patient is moving, thereby allowing for earlier patient mobilization.

As a patient's heart rate (HR) increases, the ST regulation pattern begins to change in a number of ways. For example, a number of ST parameters increase, such as ST measurements, average ST measurement, ST mean deviation as well as the ST variation. The aforementioned ST parameters are described in greater detail below with reference to FIG. 1A. In some instances, as the HR increases, the ST mean deviation and average ST measurement level off and begin to decrease, and the ST variation begins to level off and/or decrease and can then increase again showing typical oscillations. For a patient this can indicate cardiac stress and lead to potentially serious problems if left untreated. In addition to being linked to cardiac stress, the ST parameters can also indicate that the patient is reaching an anaerobic state. For patients having a low anaerobic threshold, entering an anaerobic state can be dangerous and lead to serious complications. Identifying cardiac stress or other abnormal patient conditions early can significantly aid in patient care, avoid serious complications, and decrease a patient's length of stay.

When a patient changes an activity, such as when a sitting patient stands and begins walking, starts cycling, or other exercise, etc., the patient enters a transition phase. During the transition phase, the HR, ST mean deviation, and ST variation are expected to increase. If the patient maintains a relatively constant level of exertion, the patient enters a steady state and the HR and ST mean deviation, and ST variation are expected to eventually reach a relatively constant level. However, if the patient maintains a relatively constant level of exertion and the HR, ST mean deviation and/or ST variation continue increasing for longer than an expected period of time, the patient may be experiencing an abnormal condition. Once again, by identifying the abnormal condition early using the patient monitor, a healthcare provider can avoid serious complications.

In addition to monitoring HR and ST regulation pattern, the patient monitor can also monitor action potential. In one embodiment, the patient monitor monitors action potential by monitoring the JT/HR ratio, which can also be normalized for a resting steady state e.g. (JT/HR)/(JT at rest/HR at rest) (either of which may be referred to as JT/HR or JT/HR ratio). As HR increases, the JT/HR ratio is expected to increase and eventually level off. However, for some patients, as HR increases the JT/HR ratio deviates from an expected increase or levels off and starts to decrease at a lower heart rate than expected. If the deviation is greater than a threshold value, or levels off before a threshold heart rate, the patient monitor can indicate that the patient is under stress. If left untreated, the patient's condition can lead to serious complications including death. By monitoring the action potential of a patient over time, the patient monitor can indicate an abnormal condition earlier in time and avoid serious complications.

In addition, the patient monitor is able to noninvasively determine an athlete's anaerobic threshold. As mentioned above, a patient entering an anaerobic state can be dangerous. Upon increasing the patients level of exertion, (e.g., walking, going up the stairs, exercising, etc.), the muscle metaboreflex is activated to adopt cardiac work and circulation. Just before the anaerobic state is reached, and due to an insufficient oxygen supply to the working muscle, the activity and regulation intensity of muscle metaboreflex courses the heart contraction force, leading stroke volume to further increase, a scenario which might be critical for patients. On the other hand, an athlete exercising is expected to eventually reach an anaerobic state as the level of exertion increases. The patient monitor can noninvasively determine the athlete's anaerobic threshold, allowing the athlete to determine an appropriate exercise regime without using complicated and time consuming blood tests.

FIG. 1A is a schematic diagram of an embodiment of an electrocardiogram (ECG) waveform. An ECG waveform, or ECG complex, typically includes five deflection points, labeled P, Q, R, S, and T. The first deflection, the P wave, represents atrial depolarization. The Q, R, and S deflection points are grouped together as the QRS complex 108, and represent the depolarization of the right and left ventricles of the heart. The T wave represents the repolarization of the left and right ventricles.

In addition to the deflection points P, Q, R, S and T, the ECG waveform also includes a number different intervals and segments, including the PR Interval 110, the PR segment 112, the QT Interval 114, and the ST segment 116. The PR Interval 110 is measured from the beginning of the P wave to the beginning of the QRS complex 108. The PR Interval 110 reflects the time an electrical impulse takes to travel from the sinus node through the AV node and enter the ventricles. The PR segment 112 connects the P wave and the QRS complex 108, which coincides with the electrical conduction from the AV node to the bundle of His, also known as the AV bundle, to the bundle branches and then to the Purkinje fibers. In an embodiment, the PR segment 112 is isoelectric. The QT Interval 114 is measured from the beginning of the QRS complex 108 to the end of the T wave. The ST segment 116 connects the QRS complex 108 and the T wave. The ST segment 116 represents the period when the ventricles are depolarized and can also be isoelectric.

In addition to the deflection points, intervals and segments, the ECG waveform can also include the J point, which represents the point at which the QRS complex 108 finishes and the ST segment 116 begins. The J point can be used to calculate a JT period 124, which extends from the J point to the end of the T wave. The JT period 124 is heart rate (HR) dependent, and the relative JT period increases as heart rate increases. In other words, JT/HR increases as heart rate increases. The J point can also be used to measure the degree of ST segment 116 elevation or depression, which in turn can be used to calculate an ST measurement 122.

The ST measurement 122 of the ECG waveform can be calculated by comparing an isoelectric point of the ECG waveform to a point in the ST segment 116, or an ST point. In an embodiment, the electric potential between isoelectric and the ST point is calculated. In an embodiment, the isoelectric point used to calculate the ST measurement 122 is located in the PR segment 112 of the ECG waveform and the ST point is located within the ST segment 116. In an embodiment, the ST point is a predetermined point in time after the J point, such as, for example, 60 or 80 milliseconds after the J point. Alternatively, the average of the PR segment 112, or the average of a number of points within the PR segment 112, can be used as the isoelectric point and the average of the ST segment 116, or the average of a number of points within the ST segment 116, can be used as the ST point. Other methods can be used to calculate the ST measurement 122 without departing from the spirit and scope of the description.

ST measurements are typically performed on individual ECG leads. The different ST measurements from various ECG leads can be combined to form an average ST measurement. An average ST measurement of a person at rest is approximately zero but can vary from person to person. For example an average ST measurement for one patient may be 0.4 or 0.8 and for another 1.0. Athletes can have a higher ST measurement in selected ECG leads, such as 2.0, or even higher. Elevated ST measurements can also be referred to as early repolarization. In addition to varying from person to person, the average ST measurement varies over time generating a characteristic ST regulation pattern. The variance between a current average ST measurement and a single ST measurement can be referred to as ST variation. The ST variation can swing above and below the average ST measurement as either a large or small variation. Alternatively, the ST variation can be calculated as the standard deviation of multiple ST measurements over a predefined period of time. Furthermore, as the heart rate increases, average ST measurements, as well as the size, or amplitude, of the ST variation increases as well. For example, an average ST measurement of 0.0 of a person with a heart rate of 70 bpm may exhibit ST variations of about +/−0.2. As mentioned, as the heart rate increases, the average ST measurement and the amplitude of the ST variation increase as well. For example, at a heart rate of 120 bpm, the average ST measurement may rise to 0.7 with individual ST measurements ranging from about 0.2 to about 1.2 i.e. an ST variation of about +/−0.5. Alternatively, the standard deviation of multiple ST measurements can be used as the ST variation, which may result in a calculated ST variation of 0.4 or 0.5, etc. The deviation between a current average ST measurement and a resting average ST measurement can be referred to as an ST mean deviation. Thus, in the previous example, the ST mean deviation at 70 bpm is 0 and the ST mean deviation at 120 bpm is 0.7.

Although FIG. 1A illustrates a typical ECG waveform of a patient, ECG waveforms can vary significantly from person to person. For example, not all deflection points can be seen in each ECG waveform. In addition, the ST segment as well as other parts of the ECG waveform can vary from person to person. For example, as mentioned above, the ST segment of a healthy individual at rest, such as an athlete, may be higher than the ST segment of an average person at rest. The dotted line labeled ST segment' 118 illustrates an example of an individual with an elevated ST segment, or early repolarization. In addition, when the heart is under stress or for a person experiencing heart problems, the ST segment may be lower than a normal ST segment, or depressed. The dashed line labeled ST segment "120 illustrates a depressed ST segment.

Figure 1B:
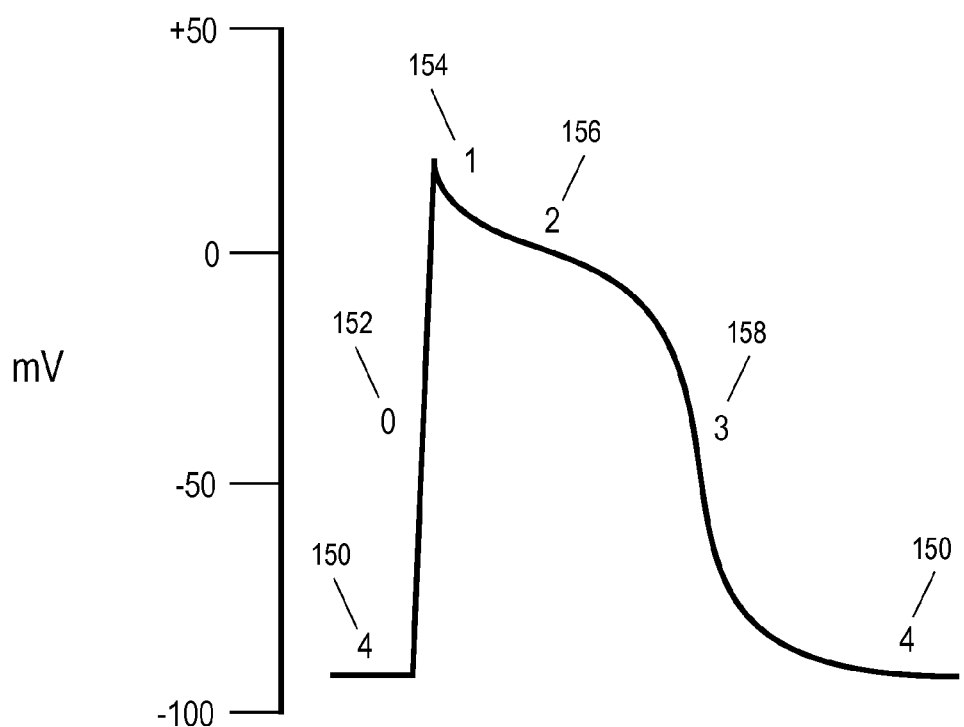
FIG. 1B is a diagram illustrative of an embodiment of a cardiac action potential of a heart cell.

FIG. 1B is a diagram illustrative of an embodiment of the cardiac action potential of a heart cell. The cardiac action potential plays a role in determining the strength of a cardiac contraction, and is typically divided into four different phases.

Phase 4 150 occurs at the resting cell membrane potential. The cell remains in Phase 4 150 until it is stimulated by an external electrical stimulus (typically an adjacent cell). In addition, certain cells of the heart have the ability to undergo spontaneous depolarization, in which an action potential is generated without any influence from nearby cells.

Phase 0 152 is the rapid depolarization phase. This phase is due to the opening of Sodium channels in the cell membrane causing a rapid increase in the membrane conductance to Sodium and thus a rapid influx of Sodium ions into the cell, leading to an inward current.

Phase 1 154 of the action potential occurs with the inactivation of the Sodium channels. The transient net outward current, which causes the small downward deflection of the action potential is due to the outward movement of potassium and chloride ions.

Phase 2 156 is the "plateau" phase of the cardiac action potential, and is sustained by a balance between inward movement of Calcium through Calcium channels and the outward movement of potassium through potassium channels. The plateau in the cardiac action potential roughly corresponds to the ST segment of the ECG waveform.

During phase 3 158 (the "rapid repolarization" phase) of the cardiac action potential, the Calcium channels close, while the Potassium channels remain open. This ensures a net outward current, corresponding to negative change in membrane potential, thus allowing more types of Potassium channels to open. The net outward, positive current (equal to loss of positive charge from the cell) causes the cell to repolarize. The Potassium channels close as the membrane potential approaches the resting membrane potential and Phase 4 150.

The amplitude, plateau slope, and duration of the cardiac action potential determine opening size and time of the voltage controlled Calcium channels in the heart cells. A larger voltage leads to an increased Calcium channel size, and relative increase in the time duration of the channel opening. The increased Calcium channel size and duration leads to a stronger heart contraction. As the heart rate of a patient increases, the cardiac action potential also increases, leading to stronger heart contractions. At a lower heart rate in a healthy person, the relative duration of the action potential increases first, followed by the action potential amplitude. As the heart rate further increases, the action potential amplitude increases faster whereas the relative duration increases by less. Just before the anaerobic state is reached, the activity of peripheral muscle reflex courses regulation intensity to increase, improving heart pumping, due to a better synchronization of cardiac action potentials.

Figure 2A:
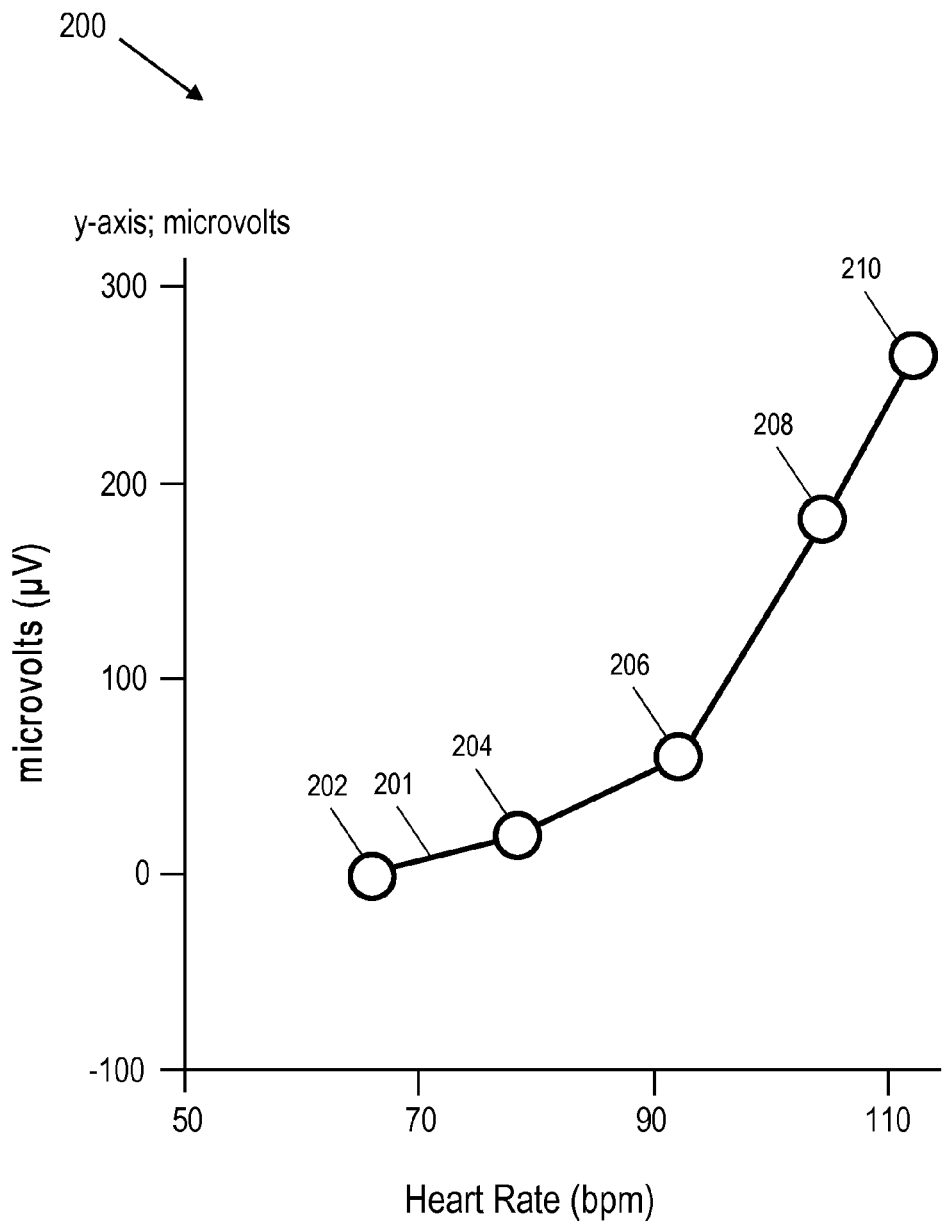
FIG. 2A is a plot diagram illustrating a graph of an embodiment of a normalized average ST measurement as a function of heart rate.

FIG. 2A is a plot diagram illustrating a graph 200 of an embodiment of a normalized average ST measurement displayed as a function of heart rate. The x-axis of the graph 200 is the heart rate of a patient. The y-axis of the graph 200 is an ST mean deviation compared to rest of patients in microvolts. The points 202, 204, 206, 208 and 210 represent various steady states of a patient. The line 201 represents the change in the ST measurement as a function of heart rate.

The steady state 202 represents a resting steady state normalized to zero. However, individual average ST measurements of patients at rest can vary considerably, as discussed above. As an example, and not to be construed as limiting, the resting steady state may be, for example, when a patient is sitting or lying down. During the resting steady state, the patient's heart rate may be between 60 to 70 beats per minute (bpm), the average ST measurement may be 0.2, and the ST variation may be 0.3 (i.e. +/−0.3). The ST mean deviation would be 0.

Upon increasing the patient's level of exertion, such as, for example, walking, the patient enters a transient state. During the transient state, the heart rate and the ST mean deviation increase. As the heart rate and ST mean deviation increase, the ST variation amplitude increases as well. If the patient maintains the new level of exertion, such as, for example, continuing to walk at a relatively constant level of exertion, a new steady state is reached, as indicated by point 204.

Upon reaching the new steady state 204, the heart rate, the ST mean deviation, and the ST variation amplitude reach a relatively constant level, which is higher than the levels at the resting steady state. For example, the heart rate at the steady state 204 can be approximately 80 bpm, the average ST measurement can be 0.3, the ST variation can be 0.4, and the ST mean deviation can be 0.1. The patient can remain in the new steady state 204 as long as the level of exertion is maintained at an approximately constant level. However, if the patient increases their level of exertion, e.g. walking faster, running, going up the stairs, cycling, etc., additional transient states and steady states can be reached, such as steady states 206, 208, and 210. During each transient state between the steady states 206, 208, and 210, the heart rate, the average ST measurement, the ST mean deviation, and the ST variation amplitude increase until the new steady state is reached. At each new steady state the heart rate, the average ST measurement, the ST mean deviation, and the ST variation amplitude reach a new level. Eventually, a level of exertion can be reached where the heart rate continues to increase, the average ST measurement and the ST mean deviation decrease, and the ST variation levels off and/or decreases and later can again temporarily increase, showing a down sloping trend.

The slope of the line 201, or increase in the average ST measurement between steady states, varies depending on the steady state. Between steady states 202 and 204, when the heart rate increases from approximately 70 bpm to approximately 80 bpm, and between steady states 204 and 206, when the heart rate increases from approximately 80 bpm to approximately 95 bpm, the slope of the line 201 is relatively small. A much larger slope is observed between the steady state 206 and the steady state 208, when the heart rate increases from approximately 95 bpm to approximately 105 bpm, and again when the heart rate increases to approximately 115 bpm at steady state 210. Eventually, as the heart rate continues to increase, the slope of the line 201 can begin to decrease and can eventually switch from a positive slope to a negative slope, which is an abnormal condition.

The graph 200 can be used by a patient monitor to determine expected average ST measurements and identify abnormalities based on the heart rate of the patient. Upon normalizing a patient's average ST measurement at rest, the plot 200 can be used to determine the patient's expected average ST measurement or ST mean deviation based on their current heart rate. The patient monitor can then identify any variations of the patient's average ST measurement or ST mean deviation from the expected average ST measurement or expected ST mean deviation. Upon identifying variations that fall outside a predetermined threshold, the patient monitor can indicate an abnormality and allow a healthcare provider to take appropriate action.

Figure 2B:
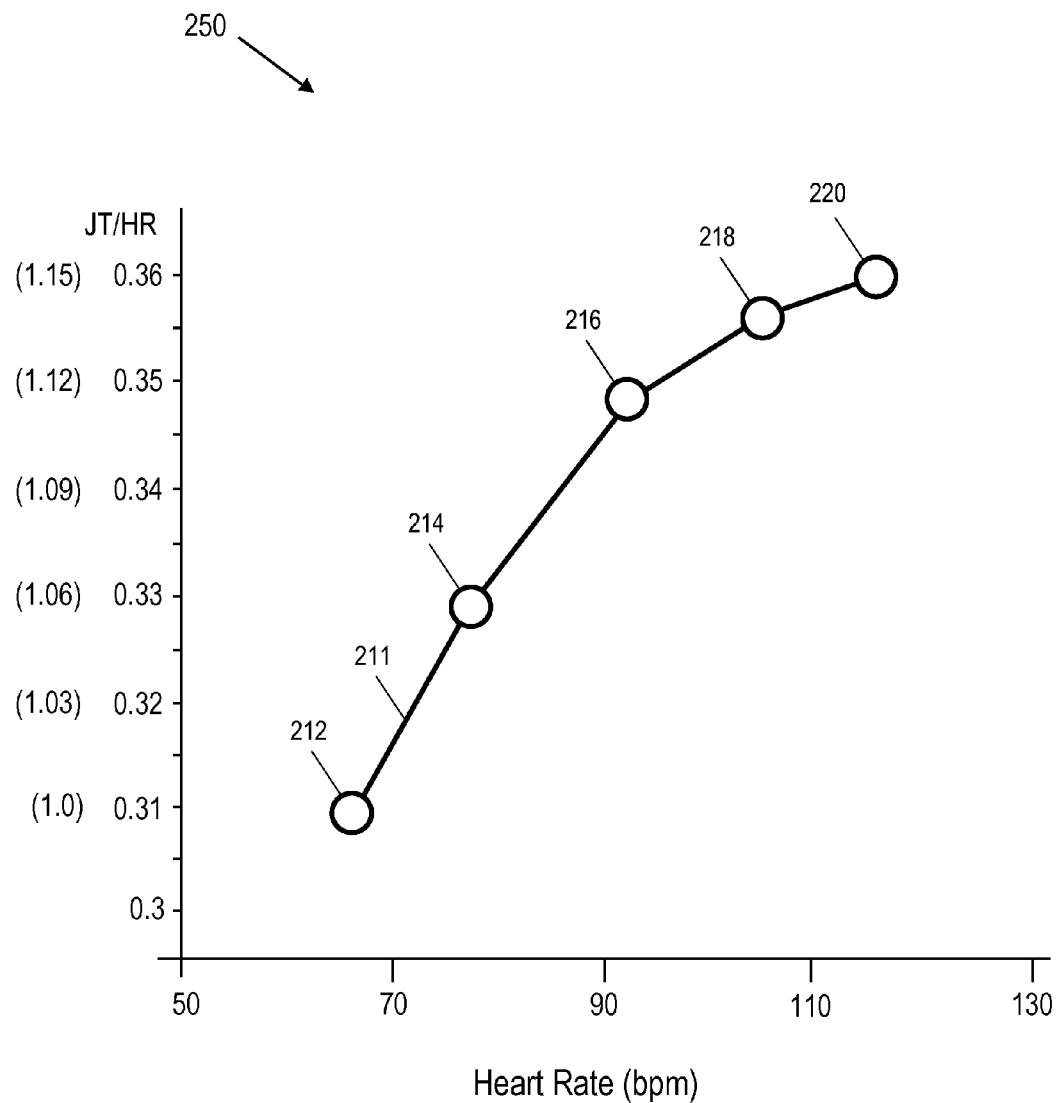
FIG. 2B is a plot diagram illustrating a graph of an embodiment of the normalized average JT/HR ratio as a function of heart rate.

FIG. 2B is a plot diagram illustrating a graph 250 of an embodiment of the normalized, average JT/HR ratio as a function of heart rate. The x-axis of the graph 250 is the heart rate of a patient. The y-axis of the graph 250 is a ratio of JT/HR. The parentheticals indicate the normalized JT/HR ratio, with the resting normalized JT/HR ratio beginning at 1.0. The points 212, 214, 216, 218, and 220 represent various steady states of a patient. The line 211 represents the change in the JT/HR ratio as a function of heart rate.

The steady state 212 represents a resting steady state. As illustrated at the steady state 212, the JT/HR ratio is ~0.31. In other words the duration of the JT period accounts for ~31% of the cardiac cycle. Although illustrated as a ratio of ~0.31, individual JT/HR ratios of patients at rest can vary considerably. As an example, and not to be construed as limiting, the resting steady state may be, for example, when a patient is sitting or lying down. During the resting steady state, the patient's heart rate may be between 60 to 70 beats per minute (bpm) and the JT/HR ratio is ~0.31. Alternatively, the graph 250 can be normalized based on a resting steady state, so that steady state 212 begins at a JT/HR ratio of 1.0.

Upon increasing the patient's level of exertion, such as, for example, walking, the patient enters a transient state. During the transient state, the heart rate and the JT/HR ratio increase. If the patient maintains the new level of exertion, such as, for example, continuing to walk at a relatively constant level of exertion, a new steady state is reached, as indicated by point 214.

Upon reaching the new steady state 214, the heart rate and JT/HR ratio reach a relatively constant level, which is higher than the levels at the resting steady state. For example, the heart rate at the steady state 214 can be approximately 80 bpm and the JT/HR ratio can increase by 6% to approximately 0.33. The patient can remain in the new steady state 214 as long as the level of exertion is maintained at an approximately constant level. However, if the patient increases their level of exertion, e.g. walking faster, running, going up stairs, cycling, etc., additional transient states and steady states can be reached, such as steady states 216, 218, and 220. During each transient state between the steady states 216, 218, and 220, the heart rate and JT/HR ratio increase until the new steady state is reached. At each new steady state the heart rate and JT/HR ratio reach a new level. Eventually, a level of exertion can be reached where the heart rate continues to increase and the JT/HR ratio levels off and start decreasing.

The slope of the line 250, or increase in the JT/HR ratio between steady states, varies depending on the steady state. Between steady states 212 and 214, when the heart rate increases from approximately 70 bpm to approximately 80 bpm, and between steady states 214 and 216, when the heart rate increases from approximately 80 bpm to approximately 90 bpm, the slope of the line 211 is relatively large. A much smaller slope is observed between the steady states 216 and 218 and the steady states 218 and 220. Thus, as the heart rate increases, the relative increase in the JT/HR ratio levels off at approximately 15% or 0.36.

The graph 250 can be used by a patient monitor to determine expected JT/HR ratios and identify abnormalities based on the heart rate of the patient. In an embodiment, the change in slopes between steady states can be used to detect abnormal conditions. Empirical data can be used to determine expected JT/HR ratio increases in light of HR increases. Deviations from the expected JT/HR ratio in light of HR increases can be flagged as abnormal conditions. For example, if a resting patient's heart rate increases by 10 bpm without any change in level of exertion and the JT/HR increases by 5% or less, the patient monitor can determine that the patient may be experiencing an abnormal condition. It is to be understood that the threshold value of 5% is a non-limiting example and other threshold values can be used based on user-specific data, empirical data, or the like.

Figure 3:
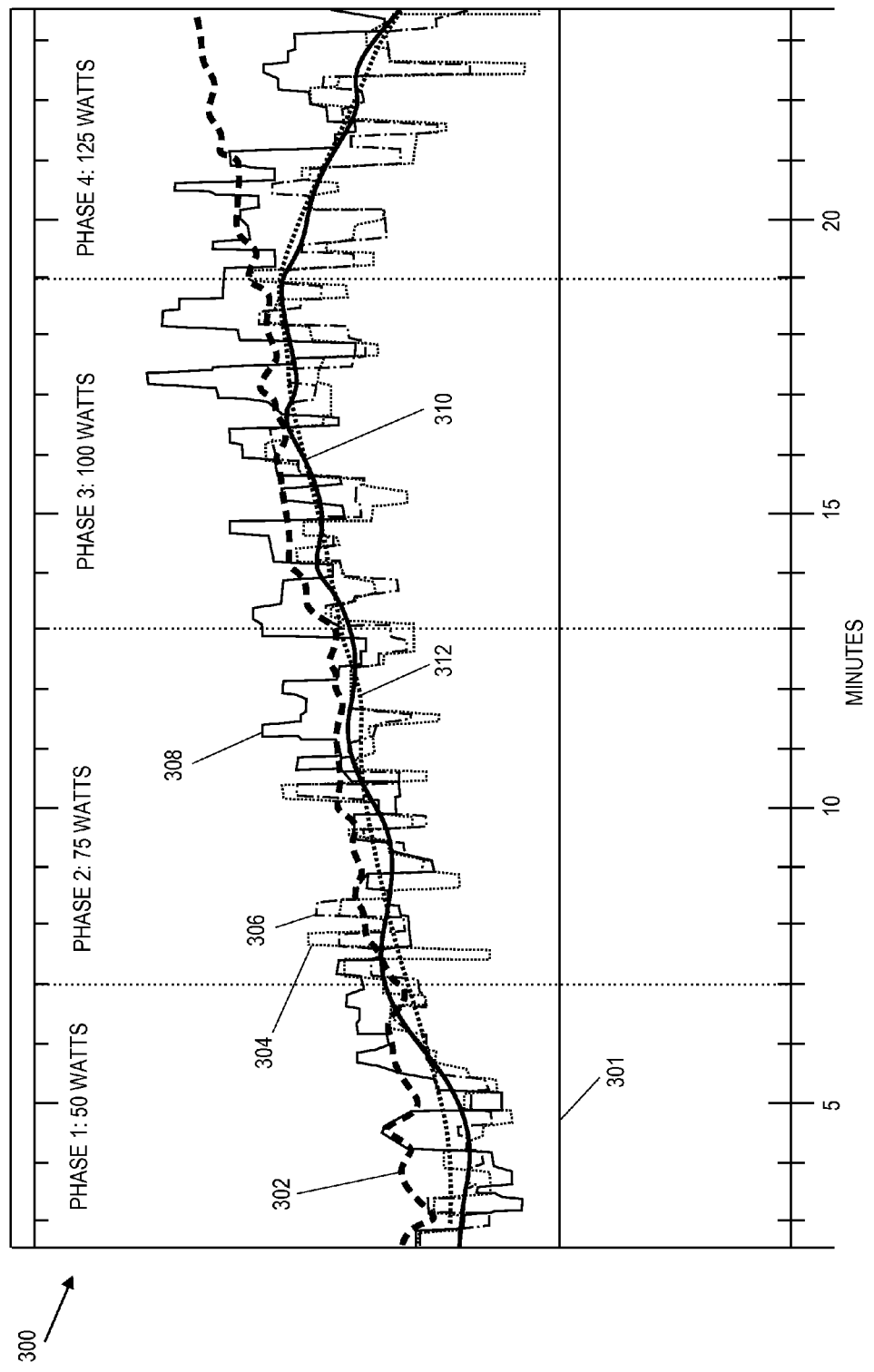
FIG. 3 is a plot diagram illustrative of a graph of an example of a patient's heart rate, ST regulation patterns, and ST mean deviation during an exercise test.

FIG. 3 is a plot diagram illustrative of a graph 300 of an example of a patient's exercise test with heart rate 302, ST regulation patterns 304, 306, 308, and the ST mean deviation 310 from the start of exercise 301 (steady state ST value at rest). The ST mean deviations 310 and 312 are the mean value of the ST regulation patterns 304, 306, 308, over time. The mean deviation 310 represents the mean deviation calculated at 60-second intervals and the mean deviation 312 represents the mean deviation calculated at 3 minute intervals. Shorter or longer time intervals can be used as desired. The ST regulation patterns 304, 306, 308 indicate measurements by three different leads and are made up of multiple ST measurements. The x-axis of graph 300 is illustrated in minutes, and the y-axis can represent heart rate or microvolt, depending on the parameter being analyzed. For example, when analyzing the heart rate 302, the y-axis represents the heart rate in beats per minute. When analyzing the ST regulation patterns 304, 306, 308, the y-axis represents microvolts.

The graph 300 is divided into four phases based on the power output of the patient. During Phase 1, the patient power output is approximately 50 watts. During Phase 2, the patient power output is approximately 75 watts. During Phases 3 and 4, the power output is 100 watts and 125 watts, respectively. The duration of each phase is 6 minutes. After one minute at rest and 6 minutes at 50 watts, Phase 2 begins at approximately 7 minutes and ends at approximately 13 minutes. Phase 3 begins at approximately 13 minutes and ends at approximately 19 minutes. Phase 4 begins at approximately 19 minutes.

The ST regulation patterns 304, 306, 308 are obtained via ECG sensors associated with a patient. Additional ECG sensors, or leads, can be used, but only three are shown for simplicity. In one embodiment, the patient monitor calculates an ST measurement for each 15-second interval for each sensor. The patient monitor calculates the ST measurement accounting for a number of variables, such as signal strength, confidence in signals, signal clarity, and the like. The calculated ST measurement is then used as representative of the entire 15-second interval. Although illustrated in 15-second intervals, alternative interval lengths can be used, such as less than 1, 5, 10, 30-second, etc. Alternatively, the ST measurements for each lead can be output as a continuous line.

In one embodiment, the ST mean deviation 310 is calculated by combining the ST measurements from the ST regulation patterns 304, 306, 308 to generate an average ST measurement. The average ST measurement can be any, or a combination, of a mean, median or mode of the different ST measurements. The ST mean deviation can be calculated using the average ST measurement, In an embodiment, the ST mean deviation is calculated by normalizing the average ST measurement, such that a resting average ST measurement is normalized to 0.

With continued reference to FIG. 3, the patient enters a transition period at the beginning of Phase 2 as the patient increases their power output to 75 watts. As explained above, during the transition period, the heart rate, average ST measurement and ST variation increase until a steady state is reached, which occurs at approximately 10 minutes. The increase in the ST variation in the individual leads is illustrated by the increase in the oscillation of the ST regulation patterns 304, 306, 308.

At the beginning of Phase 3, the patient again enters a transition period as the power output increases from 75 watts to 100 watts. During the transition period, the heart rate 302, ST mean deviation 310, and ST variation increase again. A new steady state is reached at approximately 17 minutes, at which point the heart rate 302 and ST mean deviation 310 represent a new level. Dependent on the set averaging time the mean ST deviation shows local oscillations. The oscillations represent trigger cycles of increased muscle metaboreflex activity.

A similar transition occurs as the patient enters Phase 4 and begins to output 125 watts. Similar to the previous transition periods, the heart rate increases. However, at least one distinction occurs as the patient enters Phase 4: the ST mean deviation 310 decreases. The point where heart rate 302 increases and ST mean deviation 310 decreases corresponds to a point above 110 bpm in FIG. 2A at which the line 201 levels off and begins a downward slope. Furthermore, the increase in heart rate 302 combined with the decrease in ST mean deviation 310 and leveling off of the ST variation, due to activity increase of the peripheral muscle metaboreflex triggering action potential synchronization and cardiac contraction force, can indicate that the patient is reaching an anaerobic state. For a patient producing a power output of 125 watts, the divergence of heart rate 302 and ST mean deviation 310 is expected. However, the divergence of the heart rate 302 and the ST mean deviation 310 occurring at a much lower level of exertion in patients that would otherwise be expected to be in a steady state, such as walking can indicate an abnormal condition. In these instances, identifying the divergence of heart rate 302 and ST mean deviation 310 can help a healthcare provider identify an abnormal condition and provide appropriate care to the patient. Furthermore, as heart rate increases, identifying a leveling off and/or decrease in the ST variation followed by an increase can also be used to indicate that the patient is reaching an anaerobic state.

Figure 4:
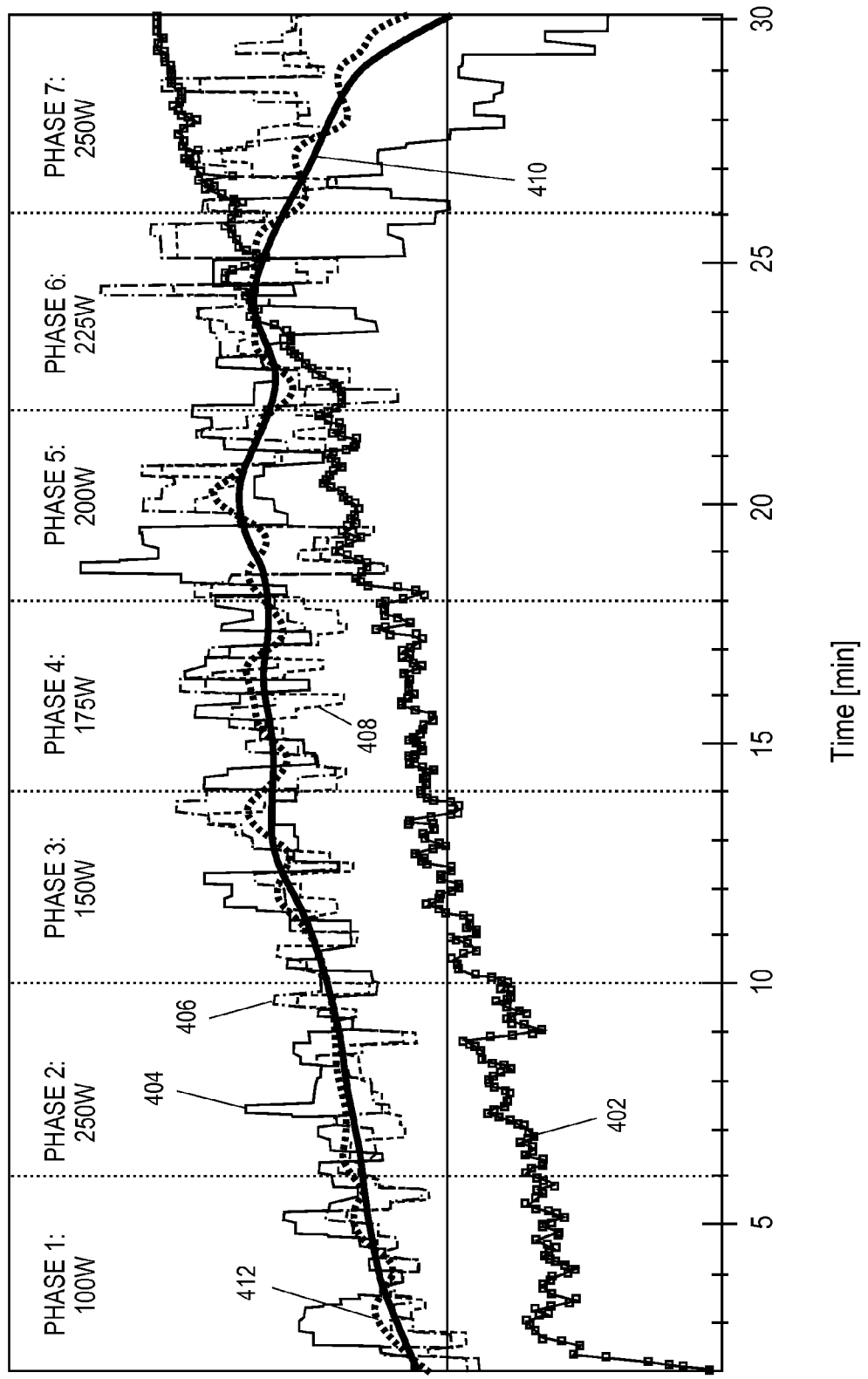
FIG. 4 is a plot diagram illustrative of a graph of an example of a patient's heart rate, ST regulation patterns, and ST mean deviation during an exercise test.

FIG. 4 is a plot diagram illustrative of graph 400, which is an example of a user's exercise test from 100 to 250 watts, similar to the graph 300 of FIG. 3. Similar to graph 300, graph 400 includes heart rate 402, ST regulation patterns 404, 406, 408, and the ST mean deviations 410, 412 from the start of exercise with the steady state ST value at rest 401.

The longer 3-minute average of mean ST deviation 412 provides a global test overview. The user goes from the pure aerobic phase (100-150 watts) to a mixed aerobic and anaerobic phase (175-225 watt) when oscillations of mean ST deviation starts to increase, and then enters the anaerobic phase (225 watts) when the ST slope turns permanently negative after approximately 26 minutes.

The one minute average of mean ST deviation in graph 450 provides a more detailed overview with prominent trigger cycles of muscle metaboreflex. A one minute average can be selected to highlight multiple cycles (time intervals) in regulation pattern with increased reflex activity used for further processing. The intensity of muscle metaboreflex can be triggered by increased metabolism e.g. accumulation of lactic acid in the working muscle. As metabolic level increases metaboreflex intensity provides feedback to the heart to increase cardiac work. With each cycle, the local negative slope of ΔST increases and at the same time the ΔHR decreases. The ΔST over this period can be divided by ΔHR to derive ST/HR slope in FIG. 5.

Figure 5:
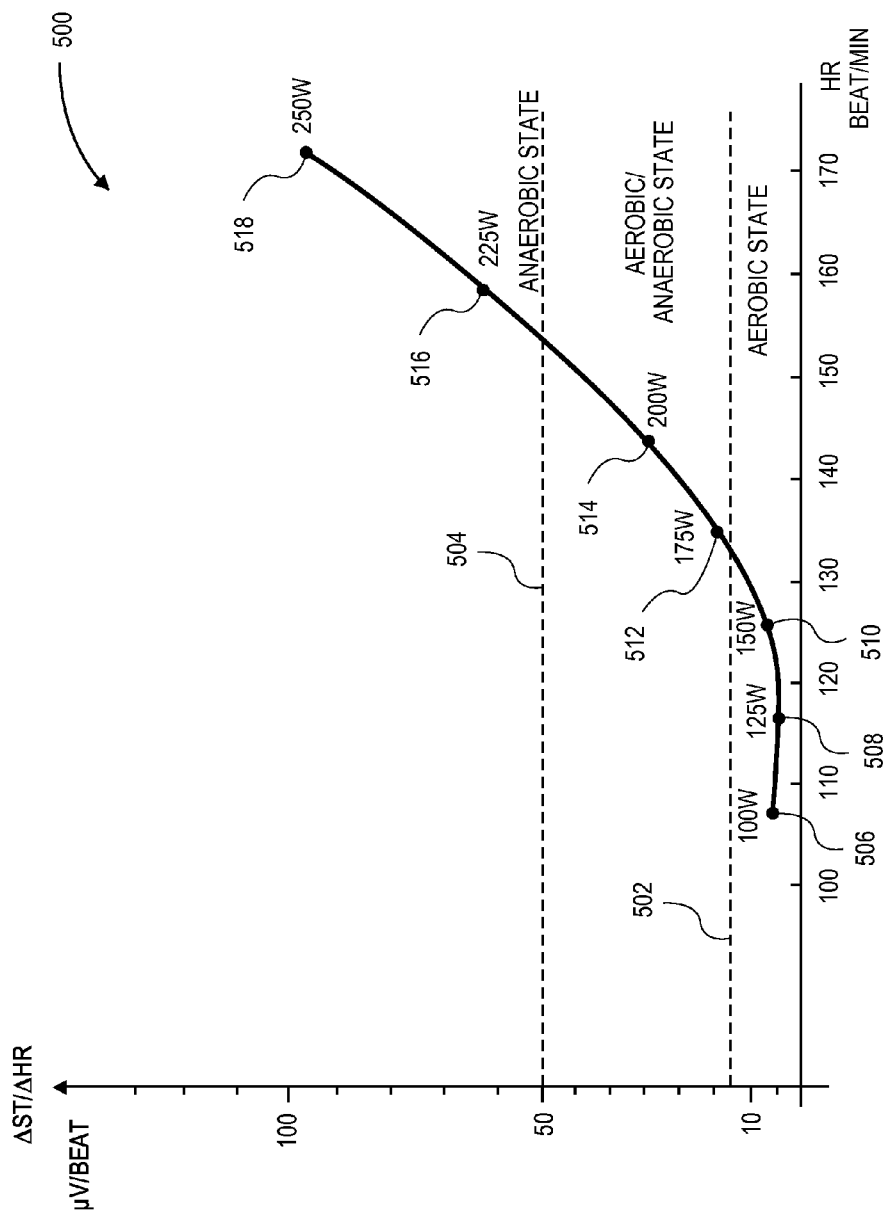
FIG. 5 is a plot diagram illustrating a graph of an embodiment of the change in the ratio of ST/HR as a function of heart rate.

FIG. 5 is a diagram illustrative of graph 500, where the ST/HR slope (or ΔST/ΔHR slope) is plotted over heart rate. The x-axis of the graph 500 is the heart rate of a patient. The y-axis of the graph 500 is ST/HR (or ΔST/ΔHR slope). The lower dashed line 502 indicates the point when a patient transitions from an aerobic state to an aerobic/anaerobic state based on the ST/HR slope. The upper dashed line 504 indicates the point when a patient transitions from the aerobic/anaerobic to an anaerobic state based on the ST/HR slope. The points 506, 508, 510, 512, 514, 516, 518 represent the power output of the patient during an exercise test, as described in greater detail above with reference to FIGS. 3 and 4. For example, at point 506 the patient's power output is 100 W, at point 510 the patient's power output (and corresponding level of exertion) has increased to 150 W.

A workload increases, the slope of each metaboreflex cycle "time interval" increases and the range of HR variation decreases. The slope correlates with metabolic accumulation, and can be used to identify a patient's transition from an aerobic state to an aerobic/anaerobic state and from the aerobic/anaerobic state to an anaerobic state. The transition from the aerobic state to the aerobic/anaerobic state can be identified when the ST/HR value is between approximately 10-15 (e.g., 10±2 and 15±2). Similarly, the transition from the aerobic/anaerobic state to the anaerobic state can be identified when the ST/HR value is between approximately 40-50 (e.g., 40±5 and 50±5). The threshold evaluation and transition identification can be based on generalized data from many patients or can be specially calibrated for patients based on previous measurements.

Accordingly, in some embodiments, a patient monitor can monitor the ST/HR value and indicate when the patient transitions from the aerobic state to the aerobic/anaerobic state, such as when the ST/HR value is between approximately 10-15. Similarly, the patient monitor can indicate when the patient transitions from the aerobic/anaerobic state to the anaerobic state, such as when the ST/HR value is between approximately 40-50. In certain embodiments, the patient monitor can indicate when the patient transitions to the anaerobic state from any other state. In certain embodiments, the patient monitor can detect whether heart rate is increasing. In some embodiments, if the heart rate is not increasing, the patient monitor can disable the ability to indicate the transitions or abnormal conditions.

Figure 6A:
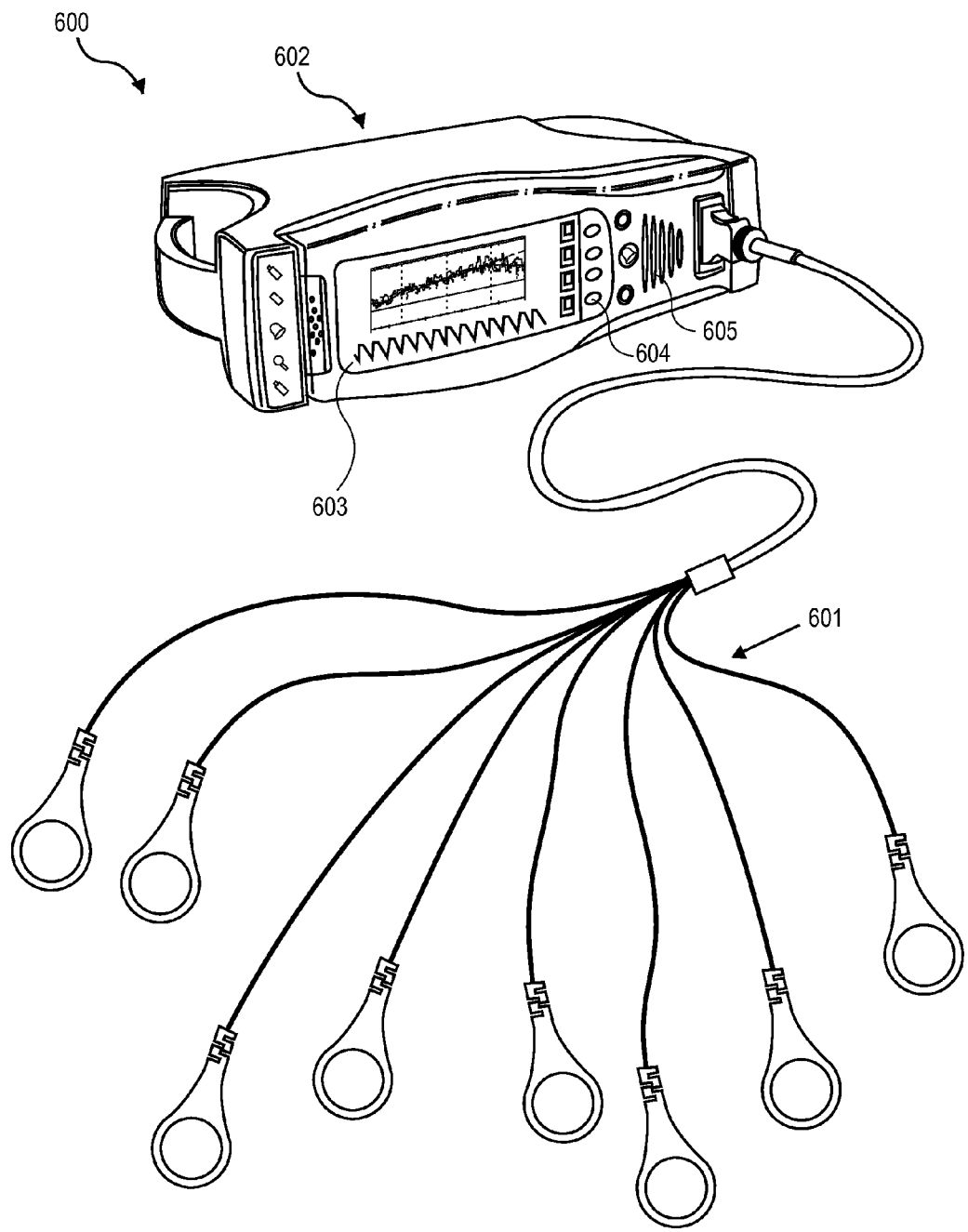
FIG. 6A illustrates an embodiment of a patient monitoring system configured to determine a patient's status based on one or more physiological parameters.

FIG. 6A illustrates an embodiment of a patient monitoring system 600 configured to determine a patient's status based on one or more physiological parameters. The physiological parameters can include, but are not limited to, ST regulation pattern, ST measurement, average ST measurement, ST mean deviation, ST oscillation pattern, ST variation, JT/HR ratio, and cardiac action potential. The patient monitoring system 600 includes a patient monitor 602 communicatively coupled to an ECG measurement system 601.

The ECG measurement system 601 can include multiple ECG sensors, or leads, associated with a patient. The ECG sensors can be attached to various locations on the patient. In one embodiment, six ECG sensors are placed on the patient's chest near the heart. Fewer or more ECG sensors can be used as desired. For example, additional sensors can be placed on the arms and legs of the patient. The ECG sensors detect electrical signals emitted by the heart and transmit ECG data representing the electrical signals to the patient monitor 602 via wired or wireless communication.

The patient monitor 602 generally includes a display 603, control buttons 604, and a speaker 605 for audible alerts. Although not illustrated in FIG. 6A, the patient monitor further includes a microprocessor for executing instructions stored within a memory device. In this manner, the microprocessor is capable of obtaining the ECG data from the ECG measurement system, processing the ECG data, and displaying the appropriate parameters on the display 603.

The display 603 is capable of displaying readings of various monitored patient parameters, which may include numerical readouts, graphical readouts, and the like. Display 603 may be a liquid crystal display (LCD), a cathode ray tube (CRT), a plasma screen, a Light Emitting Diode (LED) screen, Organic Light Emitting Diode (OLED) screen, or any other suitable display. The patient monitor 602 can monitor ECG data, including ECG complex data and ST measurement data, temperature, pulse rate, and the like. An embodiment of a patient monitoring system 600 according to the present disclosure is capable of measuring and displaying trending data of the various parameters and can conduct data analysis of the trending.

It is to be understood by one skilled in the art that the patient monitor 602 may come in various, shapes, sizes and configurations without departing from the spirit and scope of the description. For example, the patient monitor 602 may be larger, smaller, portable, comprise varying size displays 603, and the like. In addition, the patient monitor 602 can be a subset of a monitoring system capable of measuring additional physiological parameters, such as $SpO_2$, Hb, $HbO_2$, SpHb™ SpCCO®, SpOC™, SpMet®, RRa, PI, PVI®, and/or other parameters.

The patient monitor can be utilized beside for patients at rest (sitting or lying down) also for moving patients (walking or during exercise therapy etc.). When the patient changes from the resting phase into an ambulating phase the patient monitoring system will adopt new alarm limits (e.g. for HR) appropriate for the new state and help clinicians with early warning in case an abnormal condition occurs. In addition the patient monitor can compare characteristic features of the current state with reference data.

Although not illustrated in FIG. 6A, the patient monitoring system 600 can further include position and/or activity sensors (P/A sensors) to monitor the position and/or activity of the patient. The P/A sensors can include gyroscopes, accelerometers, inertial measurement units, and the like. The input from the P/A sensors can be used to determine whether the patient is at rest or moving. For example, the data from the P/A sensors can be used by the patient monitor 602 to determine whether the patient is lying or sitting down, or if the patient is moving. In an embodiment, if the patient monitor 602 determines that the patient is moving, the sensor data can further be used to determine the level of exertion of the patient, such as the rate at which the patient is moving, whether the patient is walking up or down stairs, etc.

In addition, the P/A sensors can be used by the patient monitor 602 to determine expected physiological parameter measurements and the threshold for determining an abnormal condition, which are discussed in greater detail below with reference to FIG. 7. For example, if the P/A sensor data indicates the patient is at rest, the patient monitor 602 can expect HR change associated with resting state, average ST measurement, ST mean deviation, and ST variation, and the threshold for detecting an abnormal condition can be narrowed. Conversely, if the P/A sensor data indicates the patient is moving and the rate of movement, the patient monitor 602 can expect changes in the HR, average ST measurement, ST mean deviation, and ST variation, and the threshold for detecting an abnormal condition can be increased.

In an embodiment, based on the P/A sensor data different processes can be used to detect an abnormal condition. For example, if the P/A sensor data indicates the patient is at rest, the patient monitor 602 can indicate an abnormal condition when the HR increases and an ST parameter decreases, as described in greater detail below with reference to FIG. 8. Alternatively, if the P/A sensor data indicates the patient is moving, the patient monitor can indicate an abnormal condition when an ST parameter increases for longer than a threshold period of time, as described in greater detail below with reference to FIG. 9.

FIG. 6B is a diagram illustrative of the interaction between the various components of the patient monitoring system 600 configured to determine a patient's status based on one or more physiological parameters. As mentioned previously, the patient monitoring system 600 can include an ECG measurement system 601 in communication with a patient monitor 602.

The patient monitor 602 can further include a processor for performing the various functions described herein, as well as a database or memory 644, which can include previously stored ECG data including reference ECG complex data and ST regulation pattern data. The previously stored ECG complex data and ST regulation pattern data can come from a currently monitored patient or from empirical data collected from a variety of patients. As mentioned previously, the ST regulation pattern data can include data from one or more ST regulation patterns from a variety of ECG sensors. The database 644 can store initial ECG complex data and ST regulation pattern data, HR at anaerobic threshold of a patient that can later be used as reference ECG complex data, reference ST regulation pattern data, reference HR at anaerobic treshold. To reduce repetitive processing, the database 644 can store previously extracted characteristics of the initial ECG complex data and ST regulation pattern data of a patient. In this manner, the patient monitor can use previously extracted characteristics as reference ECG complex data and reference ST regulation pattern data. In an embodiment, the initial data is obtained while the patient is at rest, such as when the patient is sitting or lying down or collected during a walk or an exercise test. Although illustrated as part of the patient monitor 602, the database 644 can be located remotely from the patient monitor 062, such as at a remote storage location at a healthcare facility, a server, etc.

The patient monitor 602 receives the ECG data including ECG complex data and ST regulation pattern data, from the ECG measurement system 601 for additional processing. As mentioned previously, the ST regulation pattern data can include data from one or more ST regulation patterns from one or more ECG sensors. In an embodiment, the patient monitor also receives position and/or activity data of the patient. In an embodiment, as part of the processing, the patient monitor 602 filters the ECG data received from the ECG measurement system 601 to remove any noise present in the data. In addition to receiving current ECG data regarding the patient, the patient monitor 602 can also receive reference ECG data, such as reference ECG complex data and reference ST regulation pattern data from the database 644. Block 606 illustrates an example of a plot of current ST regulation pattern data received from the ECG measurement system 601. Block 608 illustrates an example of a plot of reference ST regulation pattern data received from the database 644. Similarly, blocks 610 and 612 illustrate examples of current ECG complex data received from the ECG measurement system 601, and reference ECG complex data received from the database 644, respectively. As mentioned previously, in some embodiments, the reference ST regulation pattern data and reference ECG complex data received from the database 644 constitutes previously extracted characteristics.

Upon receiving the current ECG complex data and the current ST regulation pattern data, the patient monitor 602 extracts characteristics, or features, of both the ECG complex data and the ST regulation pattern data for further analysis. The patient monitor 602 extracts enough characteristics from the current ECG complex data and current ST regulation pattern to enable it to generate current action potentials and current oscillation patterns, respectively. Blocks 614-620 illustrate the extraction of the characteristics of the ECG complex data and the ST regulation pattern data.

Block 614 illustrates the extracted features from the current ST regulation pattern data received in block 606. Block 616 illustrates the extracted characteristics of the reference ST regulation pattern data. As mentioned previously, the patient monitor can extract the characteristics of the reference ST regulation pattern data dynamically, or use previously extracted characteristics received from the database 644. The extracted characteristics of the ST regulation pattern data can include any number of different characteristics. For example the extracted features can include, but are not limited to, individual ST measurements, average ST measurements, ST mean deviation, ST variation, amplitude, frequency, trend, ST and ST/HR slope, variation size, and the like. The extracted features of the ST regulation pattern found in blocks 614 and 616 can be used to generate a current ST oscillation pattern 622 and a reference ST oscillation pattern 624. The patient monitor can determine a difference and compare the generated current oscillation pattern and the generated reference oscillation pattern, as illustrated at block 634.

Similar to the extraction of features of the ST regulation pattern, at blocks 618 and 620 the patient monitor 602 extracts various characteristics from the current and reference ECG complex data. As mentioned previously, the patient monitor can extract the characteristics of the reference ECG complex data dynamically, or use previously extracted characteristics received from the database 644. The characteristics extracted from the ECG complex data can include, but are not limited to, relative time, slope, amplitude, relative duration, calcium influx duration, JT/HR ratio, action potential duration, ST point deviation, ST slope deviation, and the like. The patient monitor 402 can use the characteristics of the ECG complex data extracted in blocks 618 and 620 to generate current action potential, as illustrated in block 626, and reference action potential, as illustrated at block 628. The patient monitor can determine a difference and compare the generated current action potential and the generated reference action potential, as illustrated at block 636. The comparison 434 of the current ST oscillation pattern and reference ST oscillation pattern as well as the comparison 636 of the current action potential and the reference action potential are then processed at block 638.

A reference graph similar to the graphs 200 and 250 of FIG. 2, and illustrated at block 640, can be used to determine an expected ST measurement, expected oscillation pattern, and/or an expected action potential based on the current heart rate of the patient. In an embodiment, the current heart rate is used in combination with a reference heart rate, a reference action potential, a reference ST oscillation pattern, a reference ST measurement, and/or a reference ST regulation pattern to determine an expected action potential, an expected ST oscillation pattern, an expected ST measurement, and/or an expected ST regulation pattern. A reference graph or reference data can be used in combination with the reference heart rate and reference action potential, reference ST oscillation pattern, reference ST measurement, reference ST regulation pattern, etc. to generate an expected action potential, expected ST oscillation pattern, expected ST measurement, or expected ST regulation pattern, respectively. The reference graph or reference data can be stored in the patient monitor, or remotely, in the form of a lookup table. In an embodiment, the current heart rate and reference oscillation pattern are used to determine an expected oscillation pattern. In an embodiment, the current heart rate and reference action potential are used to determine an expected action potential. Deviations from an expected ST measurement, expected ST oscillation pattern and/or deviations from the expected action potential can then be used to indicate an abnormal condition.

The patient monitor 602 can indicate an abnormal condition in a number of different circumstances using a variety of methods. Furthermore, the P/A sensor data can be used to determine which method to use to indicate an abnormal condition. For example, in an embodiment, the patient monitor 402 indicates an abnormal condition upon detecting a heart rate increase and a decrease in amplitude of the current ST oscillation pattern from a previous or reference ST oscillation pattern. In another embodiment, the patient monitor 602 indicates an abnormal condition upon determining that the ST/HR slope is at the anaerobic threshold. In another embodiments, the patient monitor 602 indicates an abnormal condition upon determining that the current ST oscillation pattern deviates from the expected ST oscillation pattern by greater than a threshold amount. In yet another embodiment, the patient monitor 602 indicates an abnormal condition upon determining that the current action potential deviates from an expected or reference action potential by greater than a threshold amount. In an embodiment, the patient monitor compares an expected physiological parameter measurement with a current physiological parameter measurement. Based on the difference between the expected physiological parameter measurement and the current physiological parameter measurement the, the patient monitor can identify an abnormal condition. The physiological parameters can include, but are not limited to, ST regulation pattern, ST measurement, average ST measurement, ST mean deviation, ST oscillation pattern, ST variation, ST/HR slope, JT/HR ratio, other ST parameters or action potential parameters, and the like.

The patient monitor 602 can perform the various functions in a variety of ways without departing from the spirit and scope of the description. For example, upon receiving the reference ECG complex data and reference ST measurement data, the patient monitor 402 can extract the features and store a generated reference oscillation pattern and a generated action potential in the database 644. The stored information can then be compared with current oscillation patterns and current action potentials as new data is received. In this way, the patient monitor can reduce the amount of processing. As yet another example, the patient monitor can use only the ST regulation pattern data and/or the ECG complex data to identify abnormal conditions. In an embodiment, the patient monitor uses a combination of ST regulation pattern data and the ECG complex data to identify abnormal conditions.

Figure 7:
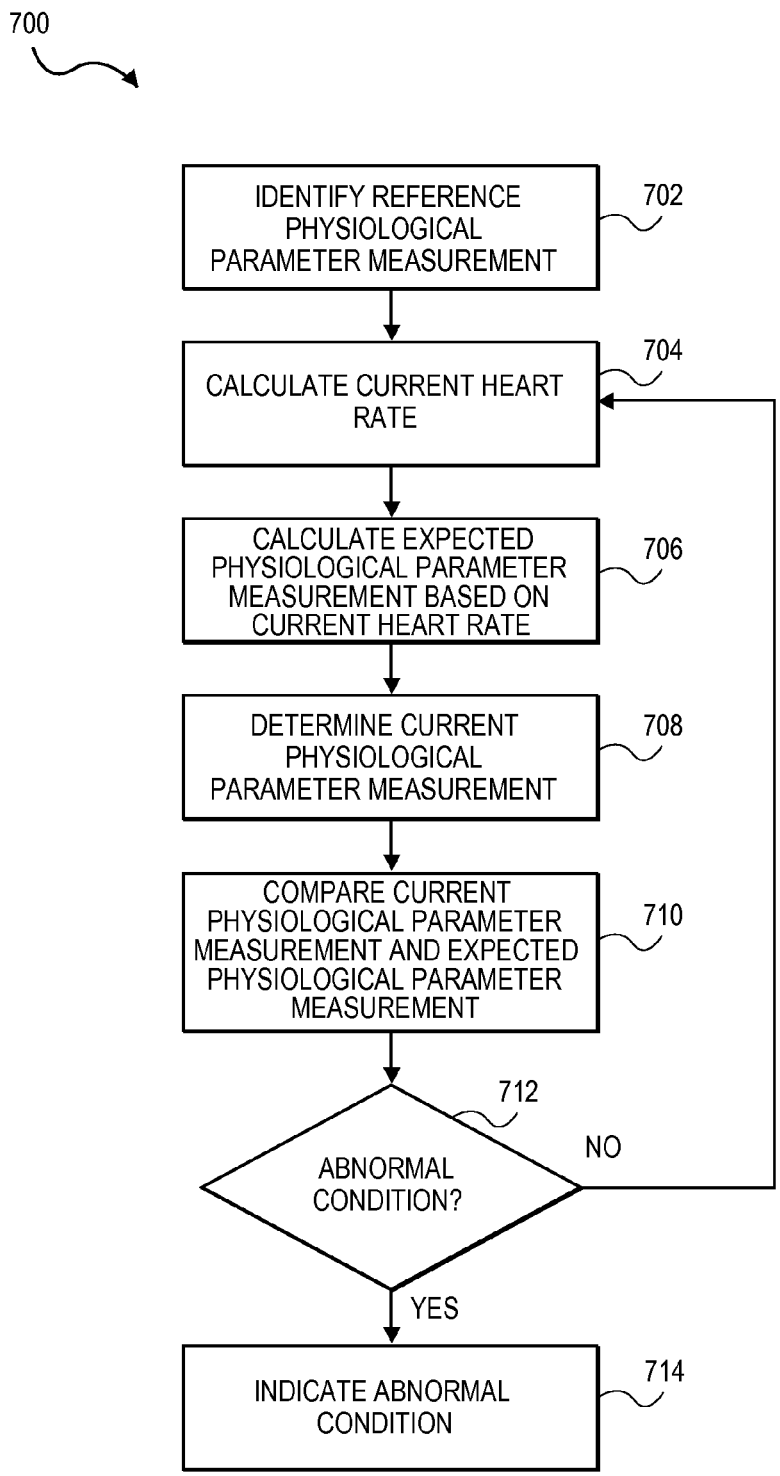
FIG. 7 is a flow diagram illustrating an embodiment of a process for indicating an abnormal patient condition using one or more physiological parameter measurements.
Figure 8:
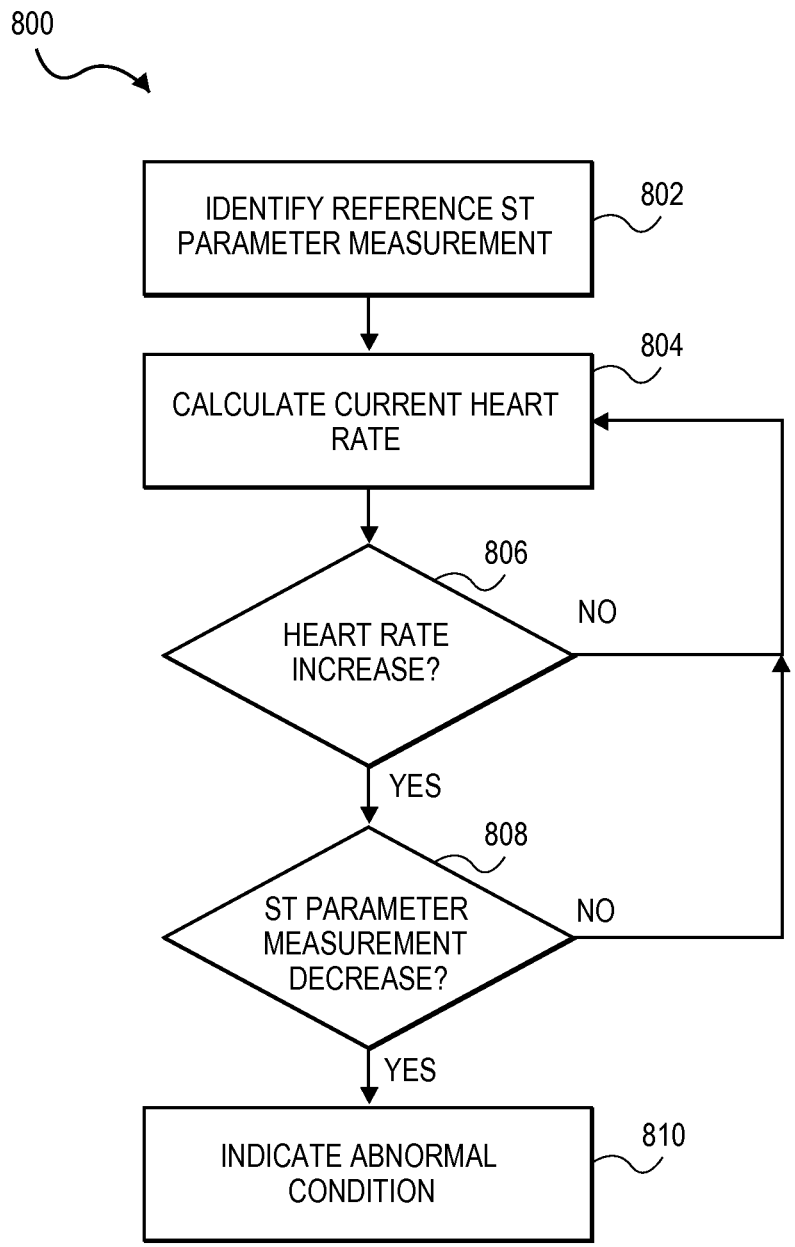
FIG. 8 is a flow diagram of a process implemented by a patient monitor for indicating an abnormal condition of a patient.
Figure 9:
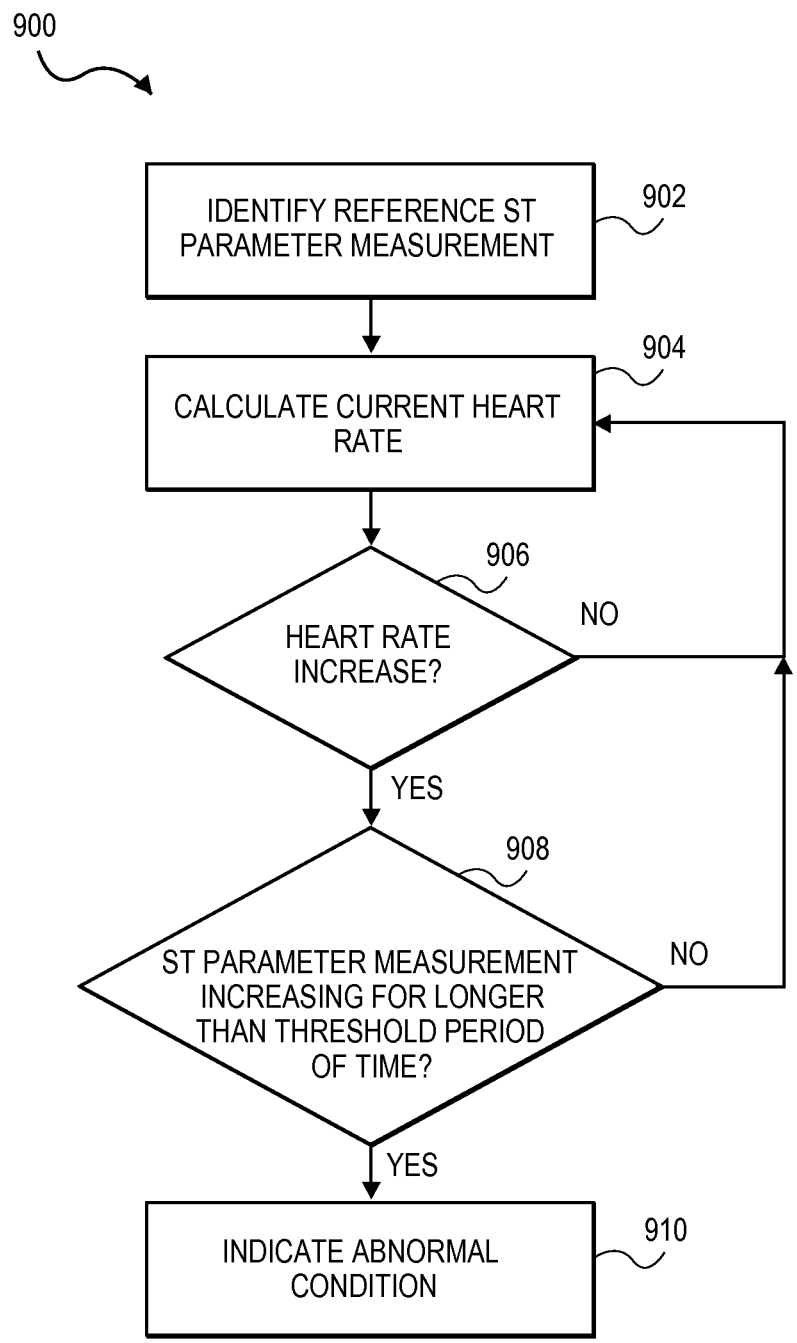
FIG. 9 is a flow diagram illustrating an embodiment of a process implemented by a patient monitor for indicating an abnormal condition of a patient.

FIGS. 7-9 are flow diagrams illustrating various embodiments of processes or routines that the patient monitor 602 can carry out using a processor. One skilled in the relevant art will appreciate that the elements outlined for the routines described below may be implemented by one or more computing devices/components that are associated with the patient monitor. Accordingly, the routines described below have been logically associated as being generally performed by the patient monitor and thus the following illustrative embodiments should not be construed as limiting.

FIG. 7 is a flow diagram illustrating an embodiment of a process 700 for indicating an abnormal patient condition using one or more physiological parameter measurements. At block 702, the patient monitor identifies one or more reference physiological parameter measurements from one or more physiological parameters of the patient. As discussed in greater detail in FIG. 6B, the reference physiological parameter measurement can be a reference action potential or action potential parameter, a reference ST oscillation pattern, a reference ST variation, a reference ST measurement, a reference average ST measurement, a reference ST mean deviation, a reference ST regulation pattern, a reference JT/HR ratio, a reference ECG complex, and the like. The reference action potential, JT/HR ratio, or other action potential parameter, including duration, Calcium influx duration, amplitude, slope, etc. can be determined by extracting characteristics of an ECG complex data received from ECG sensors during setup. Similarly, the ST parameters, including reference ST oscillation pattern, the ST variation, the reference ST variation, the reference ST measurement, the reference average ST measurement, and the reference ST mean deviation can be determined by extracting characteristics from the data of the one or more ST regulation patterns received from ECG sensors. In an embodiment, the ST parameters and action potential parameters are extracted from ECG complex data.

The reference physiological parameter measurement can be determined and identified when the patient is at rest, such as when the patient is sitting or lying down. However, the reference physiological parameter measurement can be identified at any point when the patient is in a steady state. For example, the reference physiological parameter measurement can be identified when the patient is walking.

At block 704, the patient monitor calculates the current heart rate. The patient monitor can calculate the current heart rate using ECG sensors attached to the patient or via some other patient monitoring device, such as a pulse oximeter, blood pressure monitor, plethysmograph, and the like.

At block 706, the patient monitor determines an expected physiological parameter measurement based on the current heart rate. The expected physiological parameter measurement can be calculated using any number of methods. For example, the patient monitor can use data collected from a variety of patients or from previous data from the patient. In an embodiment, the patient monitor uses the data from a graph similar to the graph 200 of FIG. 2A and graph 250 of FIG. 2B to calculate the expected physiological parameter measurement. Alternatively, or in addition, the patient monitor can use a general understanding of the trends of the physiological parameters to determine the expected physiological parameter measurement. For example, as heart rate increases the ST measurement, average ST measurement, ST mean deviation, ST variation, JT/HR, average ST measurement/HR, are expected to increase as well. Accordingly, the expected physiological parameter measurement can be a value that is greater than the reference physiological parameter measurement when the heart rate increases and less than the reference physiological parameter measurement when the heart rate decreases. In an embodiment, the expected physiological parameter measurement is the same as the reference physiological parameter.

At block 708 the patient monitor determines a current physiological parameter measurement. The current physiological parameter measurement can be determined using similar methods described above with reference to block 702. In an embodiment, the patient monitor determines the current physiological parameter measurement using current ECG complex data and/or current ST regulation pattern data. In an embodiment, the one or more current physiological parameters include action potential, ST variation, ST oscillation, ST measurement, average ST measurement, ST mean deviation, ST regulation pattern, and/or a JT/HR ratio, and the like, or any combination thereof. In an embodiment, the patient monitor extracts characteristics of a current ECG complex to calculate the current action potential and JT/HR ratio. In an embodiment, the patient monitor extracts characteristics from one or more current ST regulation patterns to calculate ST variation, ST oscillation, ST measurement, average ST measurement, and/or ST mean deviation.

At block 710 the patient monitor compares the current physiological parameter measurement with the expected physiological parameter measurement. The patient monitor can compare the current physiological parameter measurement with the expected physiological parameter measurement in a variety of ways. In an embodiment, the patient monitor compares one or more extracted characteristics, or a combination thereof, of the current physiological parameter measurement with one or more extracted characteristics, or a combination thereof, of the expected physiological parameter. For example, the patient monitor can compare the duration of the physiological parameter measurement, the amplitude, frequency, average, maximum, minimum, standard deviation, value, and the like. In an embodiment, the physiological parameter measurement is ST regulation pattern and the one or more extracted characteristics includes, but are not limited to the mean, median, or mode, the ST variation, minimum amplitude, maximum amplitude, frequency, trend, slope, an ST measurement, average ST measurement, ST mean deviation, etc. In an embodiment, the physiological parameter measurement is an action potential measurement and the one or more extracted characteristics includes, but are not limited to amplitude, ST point deviation, ST slope deviation, Calcium influx duration, JT/HR ratio, slope and the like.

At decision block 712, the patient monitor determines whether an abnormal condition is detected. The patient monitor can determine whether an abnormal condition is detected using a variety of techniques. The thresholds described below can be determined by a user, healthcare provider, and/or automatically determined by the patient monitor. Further, the thresholds can be based on user-specific data and/or empirical data. For example, the patient monitor can determine an abnormal condition has occurred based on the difference between one or more characteristics of the expected physiological parameter measurement and one or more characteristics of the current physiological parameter measurement exceeding a threshold. In an embodiment, the patient monitor determines that an abnormal condition has occurred upon determining that a current physiological parameter measurement differs from an expected physiological parameter measurement by greater than a threshold amount. In an embodiment, the patient monitor detects an abnormal condition when one or more characteristics of the current action potential differs from one or more characteristics of the expected action potential by greater than a threshold amount. For example, the current JT/HR ratio differing from the expected JT/HR ratio based on data similar to graph 250 of FIG. 2B, or the JT/HR ratio flattening prior to an expected heart rate can indicate an abnormal condition. In another embodiment, the patient monitor determines that an abnormal condition is met upon determining that the difference between one or more characteristics of the current ST regulation pattern and one or more characteristics of the expected ST regulation pattern is greater than a threshold amount. For example, an abnormal condition can be detected by a heart rate increase corresponding with the ST variation leveling off and/or decreasing and then increasing again. Alternatively, the ST mean deviation and/or average ST measurement may begin to decrease as HR increases indicating an abnormal condition.

If the patient monitor does not detect an abnormal condition, the process 700 returns to block 704 and calculates a new current heart rate. However, if the patient monitor detects an abnormal condition, the patient monitor indicates an abnormal condition has occurred, or is occurring. The abnormal condition can be indicated in a variety of ways. For example the patient monitor can sound an alarm, send a message to a health care provider, change colors or in some other way alert a health care provider.

Additional, fewer, or different blocks can be used to implement the process 700 without departing from the spirit and scope of the description. For example, upon obtaining the current hart rate data, the patient monitor can determine whether the current heart rate has changed from a previous heart rate. If no change is detected, the patient monitor can return to block 704 and calculate a new heart rate. Once a change in the heart rate is detected, the patient monitor can proceed with the remaining blocks of FIG. 7.

FIG. 8 is a flow diagram of a process 800 implemented by a patient monitor for indicating an abnormal condition of the patient. As discussed earlier, ST variation, ST mean deviation, and average ST measurement can be used to determine the condition of a patient. As heart rate increases ST variation, ST mean deviation, and average ST measurement are also expected to increase. Thus, when ST variation, ST mean deviation, and/or average ST measurement does not increase, or decreases as the heart rate increases, an abnormal condition can be identified. At block 802, the patient monitor identifies a reference ST parameter. The reference ST parameter can include ST variation, ST mean deviation, and average ST measurement. The reference ST parameter can be identified in a manner similar to that described above with reference to blocks 702 of FIG. 7.

At block 804 the patient monitor calculates a current heart rate. The patient monitor can calculate the current heart rate using a number of different techniques. For example, the patient monitor can calculate the current heart rate using data received from ECG sensors or some other sensor, such as a pulse oximeter, blood pressure device, plethysmograph data, manually, and the like.

At block 806, the patient monitor determines if the heart rate has increased from a previous heart rate. If the patient monitor determines that the heart rate has not increased from a previous heart rate, the process returns to block 804 and calculates the new current heart rate.

If the patient monitor determines that the heart rate has increased the process 800 moves to decision block 808 and the patient monitor determines whether the ST parameter has decreased. If the ST parameter has not decreased the process returns to block 804 and calculates a new current heart rate.

At block 808 if the patient monitor determines that the ST parameter has decreased, the process 800 moves to block 810 and the patient monitor indicates an abnormal condition. As described in greater detail above, the patient monitor can indicate an abnormal condition using a variety of methods. For example, the patient monitor can sound an alarm, change a screen of a patient monitor, send a message to a health care provider or in some other way indicate that an abnormal condition has been reached. In addition, using process 800, the patient monitor can identify when a patient enters an anaerobic state. As mentioned previously, it has been discovered that a leveling off of ST variation, and/or a flattening out or decrease in average ST measurement or ST mean deviation, while heart rate is increasing indicates an anaerobic state. For patients at rest in a hospital, entering an anaerobic state can lead to severe complications and even death. By identifying abnormal conditions, such as an anaerobic state, before serious complications arise, a healthcare provider can take appropriate steps to avoid harm.

In addition, identifying when a patient enters an anaerobic state can be extremely helpful for athletes. Athletes want to perform close to an anaerobic state while remaining within an aerobic state in order to maintain their level of exertion without tiring. With proper training and conditioning athletes are able increase the point at which they enter an anaerobic state. Thus, as their conditioning improves they are able to perform at higher levels of exertion while still remaining within an aerobic state. Accordingly, athletes consistently try to improve their fitness to increase the level of exertion at which they can perform while still remaining within an aerobic state.

By identifying the point at which they enter an anaerobic state, athletes can determine how to modify their training to improve their conditioning without using invasive techniques, such as blood sampling.

Additional, fewer, or different blocks can be used to implement the process 800 without departing from the spirit and scope of the description. For example, block 806 can further include whether the heart rate remains the same. In this way, an abnormal condition can be detected when the patient's heart rate remains the same, but the ST parameter measurement decreases.

FIG. 9 is a flow diagram illustrating an embodiment of a process 900 implemented by a patient monitor. At block 902 the patient monitor identifies a reference ST parameter measurement. The reference ST parameter measurement can be retrieved from ECG data received from ECG sensors attached to a patient or from a database. The ST parameter can include ST measurement, average ST measurement, ST mean deviation, and/or ST variation.

At block 904 the patient monitor calculates the current heart rate data, as described in greater detail above with reference to FIGS. 7 and 8. At block 906 the patient monitor determines whether the heart rate has increased, as discussed in greater detail above with reference to FIG. 8. If the heart rate has not increased the process 900 returns to block 904 and the patient monitor calculates a new current heart rate. However, if the heart rate has increased, the process 900 moves to block 908 and determines if the ST parameter has been increasing for longer than a threshold amount of time.

As discussed above, during the transition from one steady state to another, various ST parameters, including the ST measurement, average ST measurement, ST mean deviation, and ST variation increase. However, when a patient arrives at a steady state condition, such as when the patient is resting, continues walking at a relatively constant level of exertion, or continues to move at a relatively constant level of exertion, the ST parameters are expected to settle into a steady state condition. If the ST parameters continue to increase or deviate over a longer period of time this may indicate that the patient is suffering from an abnormal condition and additional care should be provided.

At block 908, if the patient monitor determines that the ST parameter has been increasing for longer than a threshold period of time the patient monitor moves to block 910 and indicates an abnormal condition. As discussed in greater detail above with reference to FIGS. 7 and 8 the abnormal condition can be indicated in a variety of methods. Additional, fewer, or different blocks can be used to implement the process 900 without departing from the spirit and scope of the description.

Furthermore, different processes can be used to identify an abnormal condition or an anaerobic state of a patient or user. As described in greater detail above, with reference to FIGS. 4 and 5, at a first block the ST/HR value can be monitored. In some embodiments, the ST/HR value can be monitored as heart rate increases and in certain embodiments, the ST/HR value can be monitored without regard to the heart rate. At a second block if the ST/HR value exceeds a first threshold, a warning indicator can be provided that a patient is moving from an aerobic state to an aerobic/anaerobic state. At a third block, if the ST/HR value exceeds a second threshold, the patient monitor can indicate that the patient has transitioned into an aerobic state or indicate an abnormal condition. In some embodiments, the second block can be omitted and the patient monitor can simply indicate when a user transitions to an anaerobic state or an abnormal condition.

Reference throughout this specification to "some embodiments," "certain embodiments," or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

The various illustrative logical blocks, modules, data structures, and processes described herein may be implemented as electronic hardware, computer software, or combinations of both. To clearly illustrate this interchangeability of hardware and software, various illustrative components, blocks, modules, and states have been described above generally in terms of their functionality. However, while the various modules are illustrated separately, they may share some or all of the same underlying logic or code. Certain of the logical blocks, modules, and processes described herein may instead be implemented monolithically.

The various illustrative logical blocks, modules, data structures, and processes described herein may be implemented or performed by a machine, such as a computer, a processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor may be a microprocessor, a controller, a microcontroller, a state machine, combinations of the same, or the like. A processor may also be implemented as a combination of computing devices—for example, a combination of a DSP and a microprocessor, a plurality of microprocessors or processor cores, one or more graphics or stream processors, one or more microprocessors in conjunction with a DSP, or any other such configuration.

The blocks or states of the processes described herein may be embodied directly in hardware, in a software module executed by a processor, or in a combination of the two. For example, each of the processes described above may also be embodied in, and fully automated by, software modules executed by one or more machines such as computers or computer processors. A module may reside in a computer-readable storage medium such as RAM memory, flash memory, ROM memory, EPROM memory, EEPROM memory, registers, a hard disk, a removable disk, a CD-ROM, memory capable of storing firmware, or any other form of computer-readable storage medium. An exemplary computer-readable storage medium can be coupled to a processor such that the processor can read information from, and write information to, the computer readable storage medium. In the alternative, the computer-readable storage medium may be integral to the processor. The processor and the computer-readable storage medium may reside in an ASIC.

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the logical blocks, modules, and processes illustrated may be made without departing from the spirit of the disclosure. As will be recognized, certain embodiments of the inventions described herein may be embodied within a form that does not provide all of the features and benefits set forth herein, as some features may be used or practiced separately from others.

What is claimed is:

1. A patient monitoring system, comprising:
    a plurality of electrocardiogram (ECG) sensors configured to obtain ECG data from a patient; and
    a patient monitor configured to:
        determine a reference physiological parameter measurement (PPM) of one or more physiological parameters and a first heart rate of the patient at a first time;
        determine a second heart rate of the patient at a second time;
        determine a second PPM at the second time; and
        based at least upon a determination that the second heart rate is greater than the first heart rate and the second PPM is less than the reference PPM, indicate an abnormal condition,
        wherein the one or more physiological parameters comprise at least one of an ST parameter comprising a standard deviation of a plurality of ST measurements over a time period and a JT parameter comprising JT period/heart rate.

2. The patient monitoring system of claim 1, wherein the patient monitor indicates an abnormal condition by activating an alarm.

3. The patient monitoring system of claim 1, wherein the abnormal condition comprises an anaerobic state.

4. The patient monitoring system of claim 1, wherein the one or more physiological parameters comprise the ST parameter.

5. The patient monitoring system of claim 4, wherein each ST measurement is calculated as the difference between a first point and a second point of an ECG of a heartbeat.

6. The patient monitoring system of claim 5, wherein the first point comprises an isoelectric point and the second point comprises a point in an ST segment of the heartbeat.

7. The patient monitoring system of claim 5, wherein the first point comprises a combination of points of an isoelectric segment of the heartbeat and the second point comprises a combination of points of an ST segment of the heartbeat.

8. The patient monitoring system of claim 5, wherein the first point comprises an average of an isoelectric segment of the heartbeat and the second point comprises an average of an ST segment of the heartbeat.

9. A method for determining an abnormal condition of a patient, the method comprising:
    determining using one or more processors a reference physiological parameter measurement (PPM) of one or more physiological parameters of a patient and a first heart rate based at least on ECG data obtained from one or more ECG sensors associated with the patient at a first time;
    determining a second heart rate and a second PPM at a second time based at least on ECG data obtained from the one or more ECG leads at a second time; and
    based at least upon a determination that the reference PPM is greater than the second PPM and the first heart rate is less than the second heart rate, indicating an abnormal condition, wherein
    the one or more physiological parameters comprise at least one of an ST parameter comprising a standard deviation of a plurality of ST measurements over a time period and a JT parameter comprising JT period/heart rate.

10. The method of claim 9, wherein the reference PPM is identified at a resting heart rate.

11. The method of claim 9, wherein identifying the reference PPM comprises identifying the reference PPM when the patient is in a sitting or lying down position.

12. The method of claim 9, wherein the patient monitor indicates an abnormal condition by activating an alarm.

13. The method of claim 9, wherein the one or more physiological parameters comprise the ST parameter.

14. The method of claim 13, wherein each ST measurement comprises a difference between a first point and a second point of an ECG of a heartbeat.

15. The method of claim 14, wherein the first point comprises an isoelectric point and the second point comprises a point in an ST segment of the heartbeat.

16. The method of claim 14, wherein the first point comprises a combination of points of an isoelectric segment of the heartbeat and the second point comprises a combination of points of an ST segment of the heartbeat.

17. The method of claim 14, wherein the first point comprises an average of an isoelectric segment of the heartbeat and the second point comprises an average of an ST segment of the heartbeat.

18. A patient monitoring system, comprising:
    a plurality of electrocardiogram (ECG) sensors configured to obtain ECG data from a patient; and
    a patient monitor configured to:
        determine a reference physiological parameter measurement (PPM) of one or more physiological parameters and a first heart rate of the patient at a first time;

determine a second heart rate of the patient at a second time;

determine a second PPM at the second time; and based at least upon a determination that the second heart rate is greater than the first heart rate and the second PPM is less than the reference PPM, indicate an abnormal condition, wherein the one or more physiological parameters comprise a JT parameter comprising a JT period/heart rate.

19. The system of claim 18, wherein the JT period comprises a period from an ST segment to a T wave of a heartbeat.

20. A method for determining an abnormal condition of a patient, the method comprising:

determining using one or more processors a reference physiological parameter measurement (PPM) of one or more physiological parameters of a patient and a first heart rate based at least on ECG data obtained from one or more ECG sensors associated with the patient at a first time;

determining a second heart rate and a second PPM at a second time based at least on ECG data obtained from the one or more ECG leads at a second time; and based at least upon a determination that the reference PPM is greater than the second PPM and the first heart rate is less than the second heart rate, indicating an abnormal condition, wherein the one or more physiological parameters comprise a JT parameter comprising JT period/heart rate.

21. The method of claim 20, wherein the JT period comprises a period from an ST segment to a T wave of a heartbeat.

22. A patient monitoring system, comprising:

a patient monitor communicatively coupled to a plurality of electrocardiogram (ECG) sensors configured to obtain ECG data from a patient, wherein the patient monitor is configured to:

determine a reference physiological parameter measurement (PPM) of one or more physiological parameters and a first heart rate of the patient at a first time;

determine a second heart rate of the patient at a second time;

determine a second PPM at the second time; and based at least upon a determination that the second heart rate is greater than the first heart rate and the second PPM is less than the reference PPM, indicate an abnormal condition, wherein the one or more physiological parameters comprise at least one of an ST parameter comprising a standard deviation of a plurality of ST measurements over a time period and a JT parameter comprising JT period/heart rate.

23. The patient monitoring system of claim 22, wherein the one or more physiological parameters comprise the ST parameter.

24. The patient monitoring system of claim 23, wherein each ST measurement is calculated as the difference between a first point and a second point of an ECG of a heartbeat.

25. The patient monitoring system of claim 24, wherein the first point comprises an isoelectric point and the second point comprises a point in an ST segment of the heartbeat.

26. The patient monitoring system of claim 24, wherein the first point comprises a combination of points of an isoelectric segment of the heartbeat and the second point comprises a combination of points of an ST segment of the heartbeat.

27. The patient monitoring system of claim 24, wherein the first point comprises an average of an isoelectric segment of the heartbeat and the second point comprises an average of an ST segment of the heartbeat.

28. The patient monitoring system of claim 22, wherein the one or more physiological parameters comprise the JT parameter.

\* \* \* \* \*